US 9,326,898 B2

(12) United States Patent
Kline et al.

(10) Patent No.: US 9,326,898 B2
(45) Date of Patent: May 3, 2016

(54) WEARABLE ABSORBENT ARTICLES WITH DIFFERING EAR SHAPES

(75) Inventors: Mark James Kline, Okeana, OH (US); Ronald Joseph Zink, Blue Ash, OH (US); Selin Mano Mariadhas, Madeira, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1180 days.

(21) Appl. No.: 13/315,379

(22) Filed: Dec. 9, 2011

(65) Prior Publication Data

US 2012/0157959 A1 Jun. 21, 2012

Related U.S. Application Data

(60) Provisional application No. 61/423,802, filed on Dec. 16, 2010.

(51) Int. Cl.
| | | |
|---|---|---|
| *A61F 13/15* | (2006.01) | |
| *A61F 13/20* | (2006.01) | |
| *A61F 13/49* | (2006.01) | |
| *A61F 13/56* | (2006.01) | |
| *A61F 13/58* | (2006.01) | |
| *A61F 13/62* | (2006.01) | |

(52) U.S. Cl.
CPC ....... *A61F 13/49007* (2013.01); *A61F 13/5622* (2013.01); *A61F 13/58* (2013.01); *A61F 13/62* (2013.01)

(58) Field of Classification Search
USPC .............................. 604/358, 385.3, 386, 389
See application file for complete search history.

(56) References Cited

U.S. PATENT DOCUMENTS

| | | | |
|---|---|---|---|
| 4,846,815 | A | 7/1989 | Scripps |
| 5,318,555 | A | 6/1994 | Siebers et al. |
| 5,380,313 | A | 1/1995 | Goulait et al. |
| 5,407,439 | A | 4/1995 | Goulait |
| 5,540,673 | A | 7/1996 | Thomas et al. |
| 5,542,942 | A | 8/1996 | Kline et al. |
| 5,569,233 | A | 10/1996 | Goulait |
| 5,669,900 | A | 9/1997 | Bullwinkel et al. |
| 6,156,424 | A | 12/2000 | Taylor |
| 7,867,212 | B2 * | 1/2011 | Waksmundzki et al. ..... 604/389 |

(Continued)

FOREIGN PATENT DOCUMENTS

| | | |
|---|---|---|
| WO | WO 2004/030763 | 4/2004 |
| WO | WO 2004/082918 | 9/2004 |

(Continued)

OTHER PUBLICATIONS

PCT International Search Report, mailed Mar. 14, 2012, 11 pages.

*Primary Examiner* — Michele M Kidwell
(74) *Attorney, Agent, or Firm* — Sarah M. DeCristofaro; Abbey A. Lopez; Charles R. Ware

(57) ABSTRACT

Embodiments of the present disclosure include an array of front-fastenable disposable wearable absorbent articles with differing ear shapes. Each different ear shape corresponds to a body shape and activity level for a particular wearer. In an embodiment of the present disclosure, a first article, sized for a wearer of a first size, has a first side ear with a first side ear upper edge with concave portions, and a second article, sized for a wearer of a second size that is greater than the first size, has a second side ear with a second side ear upper edge with convex portions.

19 Claims, 15 Drawing Sheets

(56) References Cited

U.S. PATENT DOCUMENTS

| | | |
|---|---|---|
| 2002/0072723 A1* | 6/2002 | Ronn et al. .................... 604/358 |
| 2003/0077430 A1 | 4/2003 | Grimm et al. |
| 2004/0044324 A1 | 3/2004 | Swenson et al. |
| 2004/0181200 A1 | 9/2004 | Desai et al. |
| 2004/0193133 A1 | 9/2004 | Desai et al. |
| 2006/0212013 A1 | 9/2006 | Cohen et al. |
| 2006/0241558 A1 | 10/2006 | Ramshak et al. |
| 2007/0016155 A1 | 1/2007 | Chang et al. |
| 2007/0142798 A1 | 6/2007 | Goodlander et al. |
| 2007/0157441 A1 | 7/2007 | Kline et al. |
| 2010/0108554 A1* | 5/2010 | Melius et al. ................. 206/438 |

FOREIGN PATENT DOCUMENTS

| | | |
|---|---|---|
| WO | WO 2005/110731 A3 | 11/2005 |
| WO | WO 2009/128029 A2 | 10/2009 |

\* cited by examiner

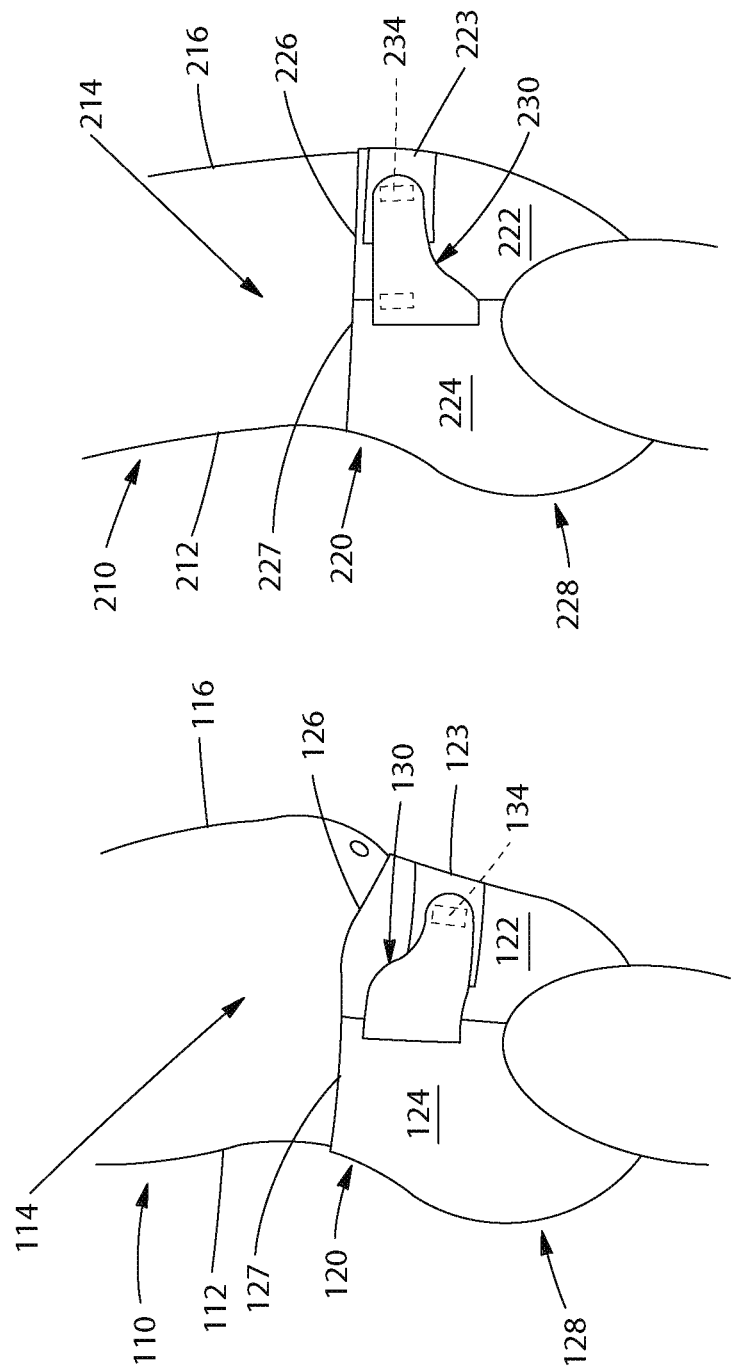

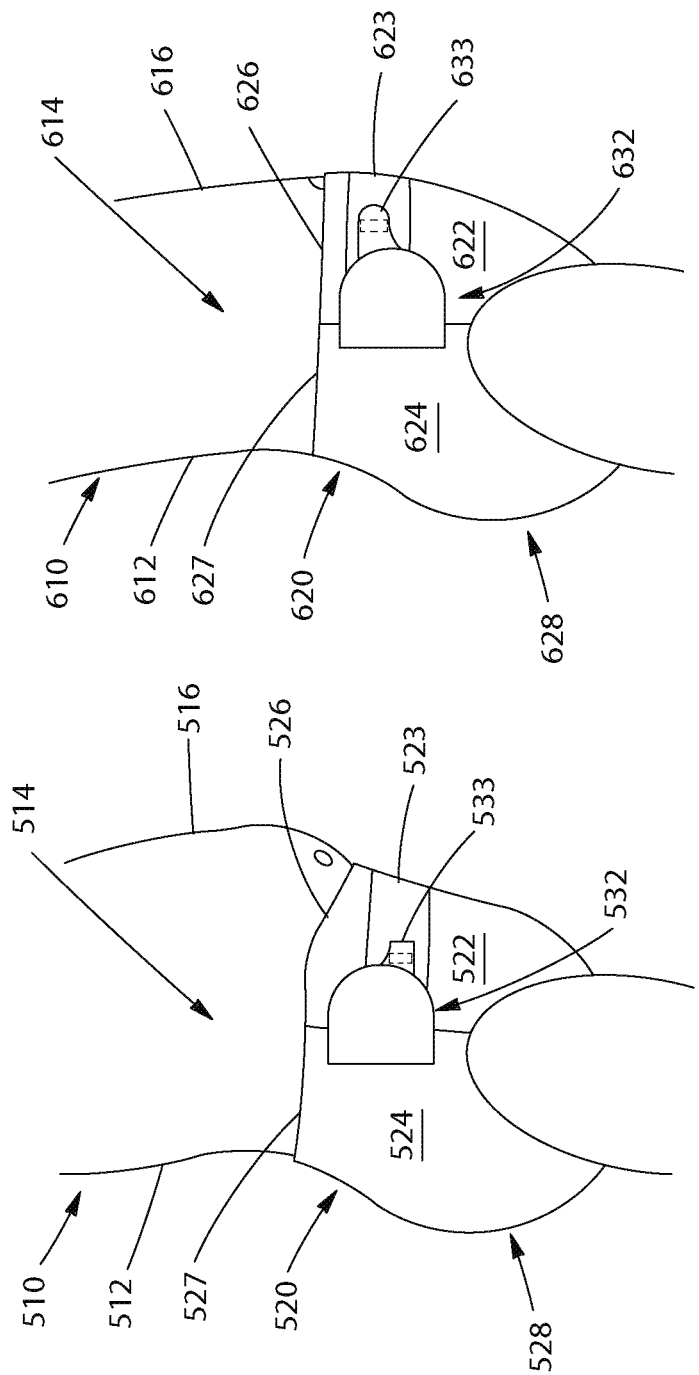

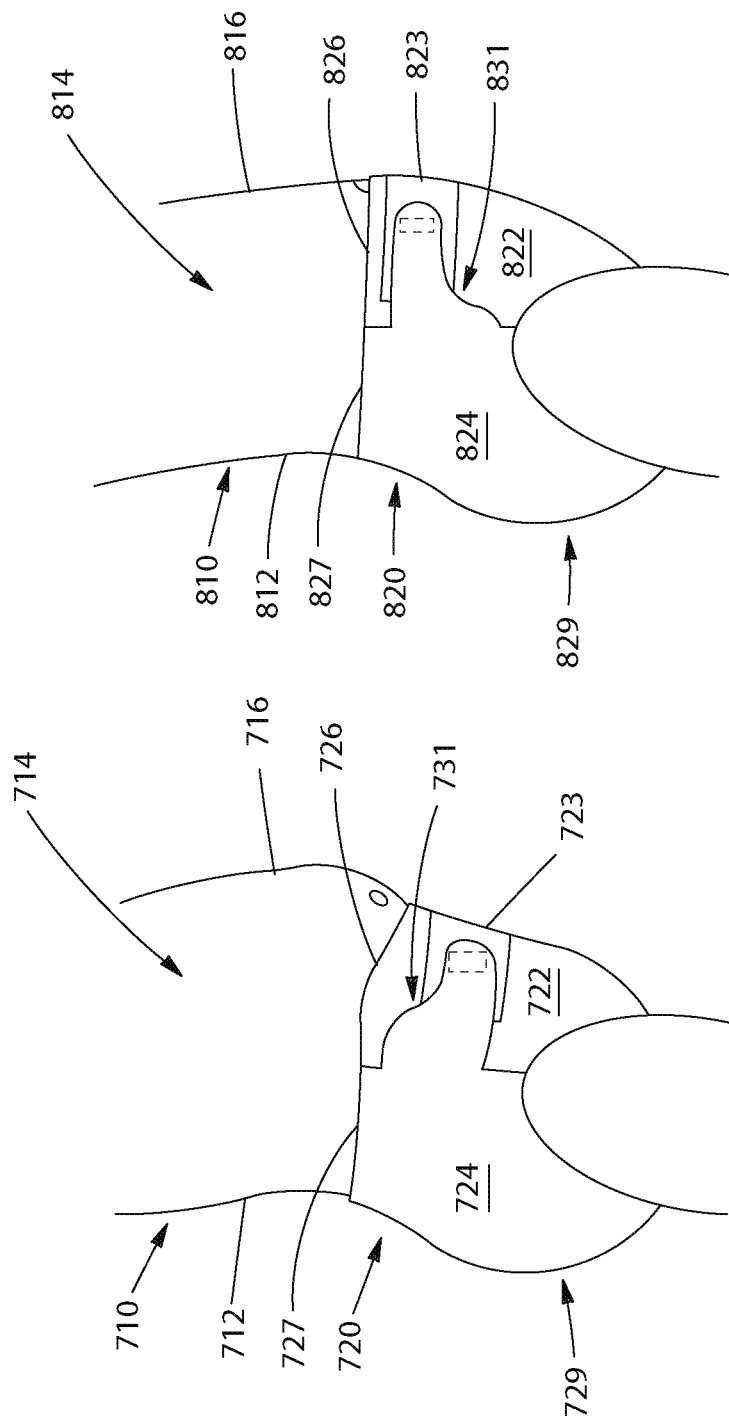

WEARABLE ABSORBENT ARTICLES WITH DIFFERING EAR SHAPES

CROSS REFERENCE TO RELATED APPLICATIONS

This application claims the benefit of U.S. Provisional Application No. 61/423,802, filed Dec. 16, 2010, which is incorporated herein by reference.

FIELD OF THE DISCLOSURE

The present disclosure generally relates to wearable absorbent articles, and more particularly relates to front-fastenable wearable absorbent articles with differing ear shapes.

BACKGROUND OF THE DISCLOSURE

Front-fastenable wearable absorbent articles for babies typically comprise a single design available in different sizes to fit a variety of wearers, ranging from newborns to active toddlers. Many article ear shapes also take the one design fits all approach. However, different sized wearers can have different body shapes and different sized wearers can have different activity levels. A single ear shape may not be appropriate for all body shapes and activity levels.

SUMMARY OF THE DISCLOSURE

The present disclosure describes arrays of front-fastenable disposable wearable absorbent articles with differing ear shapes. Each different ear shape corresponds to a body shape and activity level for a particular wearer.

In accordance with a first embodiment of the present disclosure, an array comprises a first article and a second article. The first article is a first front-fastenable disposable wearable absorbent article sized for a first wearer size. The first article includes a first side ear having a first side ear end region with a first end region upper edge portion. The first end region upper edge portion has a first end region upper edge overall lateral dimension, an inboard endpoint, and an outboard endpoint. The first end region upper edge portion also has at least one first concave portion forming a first total concave lateral dimension that is at least 25% of the first end region upper edge overall lateral dimension. From the inboard endpoint to the outboard endpoint, the first end region upper edge portion only has slopes less than or equal to zero. The second article is a second front-fastenable disposable wearable absorbent article sized for a second wearer size that is greater than the first wearer size. The second article includes a second side ear having a second side ear end region with a second end region upper edge portion. The second end region upper edge portion has a second end region upper edge overall lateral dimension. The second end region upper edge portion has at least one second convex portion forming a second total convex lateral dimension that is at least 25% of the second end region upper edge overall lateral dimension.

In accordance with a second embodiment of the present disclosure, an array comprises a first article and a second article. The first article is a first front-fastenable disposable wearable absorbent article sized for a first wearer size. The first article includes a first side ear having a first side ear end region with a first end region upper edge portion. The first end region upper edge portion has a first end region upper edge overall lateral dimension. The first end region upper edge portion has at least one first concave portion forming a first total concave lateral dimension that is at least 50% of the first end region upper edge overall lateral dimension. The second article is a second front-fastenable disposable wearable absorbent article sized for a second wearer size that is greater than the first wearer size. The second article includes a second side ear having a second side ear end region with a second end region upper edge portion. The second end region upper edge portion has a second end region upper edge overall lateral dimension. The second end region upper edge portion has at least one second convex portion forming a second total convex lateral dimension that is at least 50% of the second end region upper edge overall lateral dimension.

In accordance with a third embodiment of the present disclosure, an array comprises a first article and a second article. The first article is a first front-fastenable disposable wearable absorbent article sized for a first wearer size. The first article includes a first side ear having a first side ear end region with a first end region upper edge portion. The first end region upper edge portion has a first end region upper edge overall lateral dimension. The first end region upper edge portion has at least one first concave portion forming a first total concave lateral dimension that is at least 25% of the first end region upper edge overall lateral dimension. The first end region upper edge portion also has at least one first convex portion forming a first total convex lateral dimension that is less than 25% of the first end region upper edge overall lateral dimension. The second article is a second front-fastenable disposable wearable absorbent article sized for a second wearer size that is greater than the first wearer size. The second article includes a second side ear having a second side ear end region with a second end region upper edge portion. The second end region upper edge portion has a second end region upper edge overall lateral dimension. The second end region upper edge portion has at least one second convex portion forming a second total convex lateral dimension that is at least 25% of the second end region upper edge overall lateral dimension. The second end region upper edge portion also has at least one second concave portion forming a second total concave lateral dimension that is less than 25% of the second end region upper edge overall lateral dimension.

BRIEF DESCRIPTION OF THE DRAWINGS

FIG. 3 illustrates a side view of absorbent article of FIG. 1.

FIG. 4 illustrates a side view of absorbent article of FIG. 2.

FIG. 5 illustrates a side view of a variation of the first front-fastenable wearable absorbent article of FIG. 1, having discrete, tape-tab side ears, according to embodiments of the present disclosure.

FIG. 6 illustrates a side view of a variation of the second front-fastenable wearable absorbent article of FIG. 2, having discrete, tape-tab side ears, according to embodiments of the present disclosure.

FIG. 7 illustrates a side view of a variation of the first front-fastenable wearable absorbent article of FIG. 1, having unitary, integrally-formed side ears, according to embodiments of the present disclosure.

FIG. 8 illustrates a side view of a variation of the second front-fastenable wearable absorbent article of FIG. 2, having unitary, integrally-formed side ears, according to embodiments of the present disclosure.

DETAILED DESCRIPTION OF THE DISCLOSURE

Figure 1:
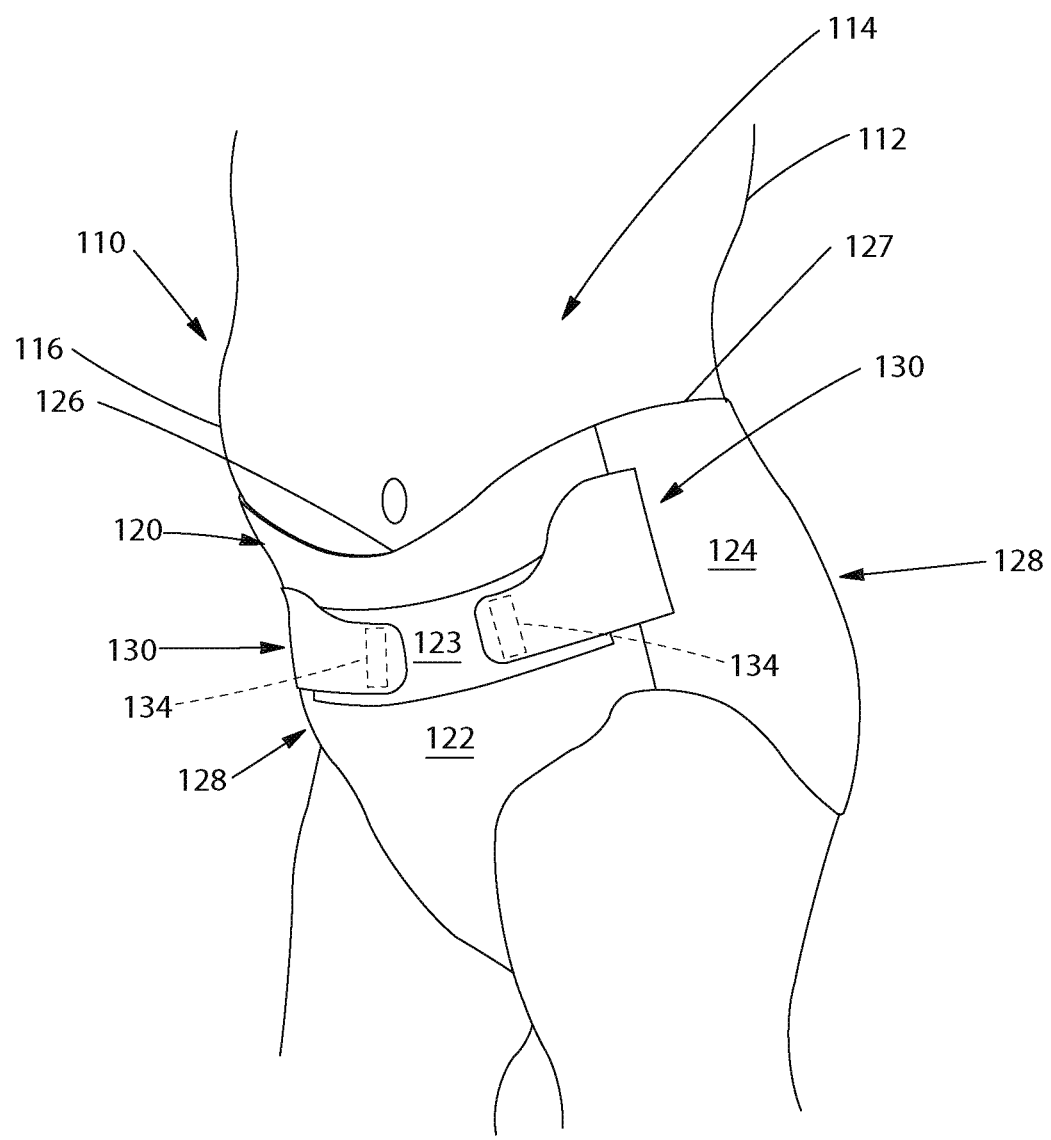
FIG. 1 illustrates a perspective view of a first front-fastenable wearable absorbent article fastened on a wearer of a first size, including discrete, integrally-formed side ears shaped to fit high on the wearer's sides and low on the belly of the first wearer, according to embodiments of the present disclosure.

The present disclosure describes arrays of front-fastenable disposable wearable absorbent articles with differing ear shapes. Each different ear shape corresponds to a body shape and activity level for a particular wearer. As a result, articles in the array provide better fit and comfort to each wearer. The arrays of the present disclosure can be applied to all kinds of wearable absorbent articles.

An absorbent article can receive and absorb bodily exudates (e.g. urine, menses, feces, etc.). Examples of absorbent articles include products for sanitary protection and hygienic use. Some absorbent articles are wearable. A wearable absorbent article is configured to be worn on or around a lower torso of a body of a wearer. Examples of wearable absorbent articles include diapers and incontinence undergarments. A wearable absorbent article can receive and contain bodily exudates while being worn by a wearer. Wearable absorbent articles can use embodiments of the present disclosure.

Some absorbent articles are disposable. A disposable absorbent article is configured to be wholly disposed of after a single use. A disposable absorbent article is configured such that the soiled article is not intended to be restored and reused (e.g., not intended to be laundered). Disposable absorbent articles can use embodiments of the present disclosure.

Some absorbent articles are reusable. A reusable absorbent article is configured to be partly or wholly used more than once. A reusable absorbent article is configured such that part or all of the article is durable, or wear-resistant to laundering, or fully launderable. One example of a reusable absorbent article is a diaper with a washable outer cover. Reusable absorbent articles can use embodiments of the present disclosure.

The figures of the present disclosure are intended to illustrate elements, their parts, and their relationships, as described in the specification; the figures are not intended to illustrate any particular relative or absolute size or dimension, unless otherwise stated in the text. The figures are not intended to illustrate all details of the articles.

Throughout the present disclosure, various figures illustrate human bodies. As a whole, these figures are intended to illustrate the presence of various external human anatomical features and general relationships between these features. These figures are not intended to teach precise details or exact proportions of the human anatomical features that are illustrated. For ease of reference, the present disclosure refers to many of these features using simple and informal terminology. These human anatomical features can relate to wearable absorbent articles, according to embodiments of the present disclosure. Some figures are intended to illustrate how such wearable absorbent articles can fit on human bodies of wearers.

In various embodiments, front-fastenable wearable absorbent articles can have side ears with shapes configured for babies, according to their stages of development. Baby stages of development may range from newborn to active toddler seeking independence. For instance, a first stage may include newborns with relatively large bellies that significantly protrude from their lower torso. Newborns may be relatively immobile. The activity level of a newborn may be as little as reflexive movement of the arms and legs, head-raising, and rolling over. An article for a wearer at a first stage of development may be size newborn or size one.

A second stage of development may include babies that are in an early mobility phase. Babies at the second stage of development have relatively moderate sized bellies that somewhat protrude from their lower torso. The activity level of a baby at a second stage of development is greater than a newborn at a first stage of development. Activities at a second stage of development may include sitting, scooting, rolling, and crawling. An article for a wearer at a second stage of development may be larger than the article for a first stage of development. For example, an article for a wearer at a second stage may be size one or size two.

A third stage of development may include babies in an active mobility phase. Babies at a third stage of development may have relatively small bellies that slightly protrude from their lower torso. The activity level of a baby at the third stage is greater than that of a baby at a second stage of development. Activities at a third stage of development may include standing, walking, and beginning to run. An article for a wearer at a third stage of development may be larger than the article for a second stage of development. For example, an article for a wearer at a third stage may be size two or size three.

A fourth stage of development may include toddlers in a pre-training phase. Toddlers at a fourth stage of development may have relatively flat bellies that do not significantly protrude from their lower torso. The activity level of a toddler at a fourth stage of development may be greater than that of a baby at a third stage of development. Activities at a fourth stage of development may include dressing and developing coordination to run and walk without falling. An article for a wearer at a fourth stage of development may be larger than the article for a third stage of development. For example, an article for a wearer at a fourth stage may be size three or larger.

In addition to these four stages, other stages of development are also contemplated. A stage of development includes at least one wearer size, but may include multiple wearer sizes. For each wearer size within a stage of development, a corresponding article may be offered.

FIG. 1 illustrates a perspective view of a first front-fastenable wearable absorbent article 120 fastened on a first wearer 110 of a first size, including first discrete, integrally-formed side ears 130 shaped to fit high at first sides 114 and low on a first belly 116 of the first wearer 110, according to embodiments of the present disclosure. The first article 120 is sized for the first wearer 110. The first wearer 110 may be of size newborn, size one, or any greater size. In the embodiment of FIG. 1, the first wearer 110 is in a first stage of development corresponding with an immobile newborn. However, in various embodiments, the first wearer 110 may be in another stage of development. The first discrete, integrally-formed side ears 130 also have upper edges with concave portions, as described in connection with the embodiment of FIG. 11. In embodiments throughout the present disclosure, a concave portion can have a fixed radius or a variable radius over its length.

The first wearer 110 has a first navel, a first back 112, the first sides 114, the first belly 116, and first legs. The first belly 116 is relatively large, for the stature of the first wearer 110. Since the first belly 116 is large, it tends to protrude significantly. The first wearer 110 is smaller than a second wearer 210 of FIG. 2. However, the first belly 116 protrudes proportionally more than a second belly 216 of the second wearer 210.

The first wearer 110 may wear an absorbent article that is smaller than an absorbent article for the second wearer 210. For example, the first wearer 110 can wear an absorbent article of size newborn while the second wearer 210 can wear an absorbent article that is size one or larger. Also for example, the first wearer 110 can wear an absorbent article of size one while the second wearer 210 can wear an absorbent article that is size two or larger.

The first wearer 110 may be at a stage of development that is earlier than a stage of development for the second wearer 210. As an example, the first wearer 110 can be at a first stage of development, while the second wearer 210 can be at a second or later stage of development. As another example, the first wearer 110 can be at a second stage of development, while the second wearer 210 can be at a third or later stage of development.

The first article 120 has a first front 122, a first back 124, a first chassis 128, and first discrete, integrally-formed side ears 130. As used herein, the term "discrete," with respect to a side ear, refers to a side ear that is a separate piece, joined to a central chassis via a bond, such as an adhesive bond, a thermal bond, or any other suitable bond or combination of bonds. As used herein, the term "integrally-formed," with respect to a side ear having an attachment area, refers to a side ear that has at least one longitudinal line along the end region, along which a layer of material forming the end region is longitudinally coextensive with a layer of material forming an extensible region. These characteristics structurally and functionally distinguish a side ear having a "tape-tab" type construction, in which a comparatively short tab member, bearing an attachment area and forming an end region of the side ear, joins a relatively longer laterally-extensible region of the side ear, in which no such longitudinal line exists.

The first front 122 has a first front waist edge 126. The first back 124 has a first back waist edge 127. The first discrete, integrally-formed side ears 130 are joined to the first back 124, extend around the first sides 114, and fasten to the first front 122 within a landing zone 123. The first discrete, integrally-formed side ears 130 have first attachment areas 134.

The first discrete, integrally-formed side ears 130 are integrally-formed. The landing zone 123 is configured so that the attachment areas 134 can fasten to the landing zone 123. In FIG. 1, the landing zone 123 is illustrated as defined area formed by a separate material, however in some embodiments of a front-fastenable disposable wearable absorbent article a separate landing zone is not required. In various embodiments, the landing zone can be rectangular, or Chevron shaped, or other shapes, as will be understood by one of skill in the art.

Figure 11:
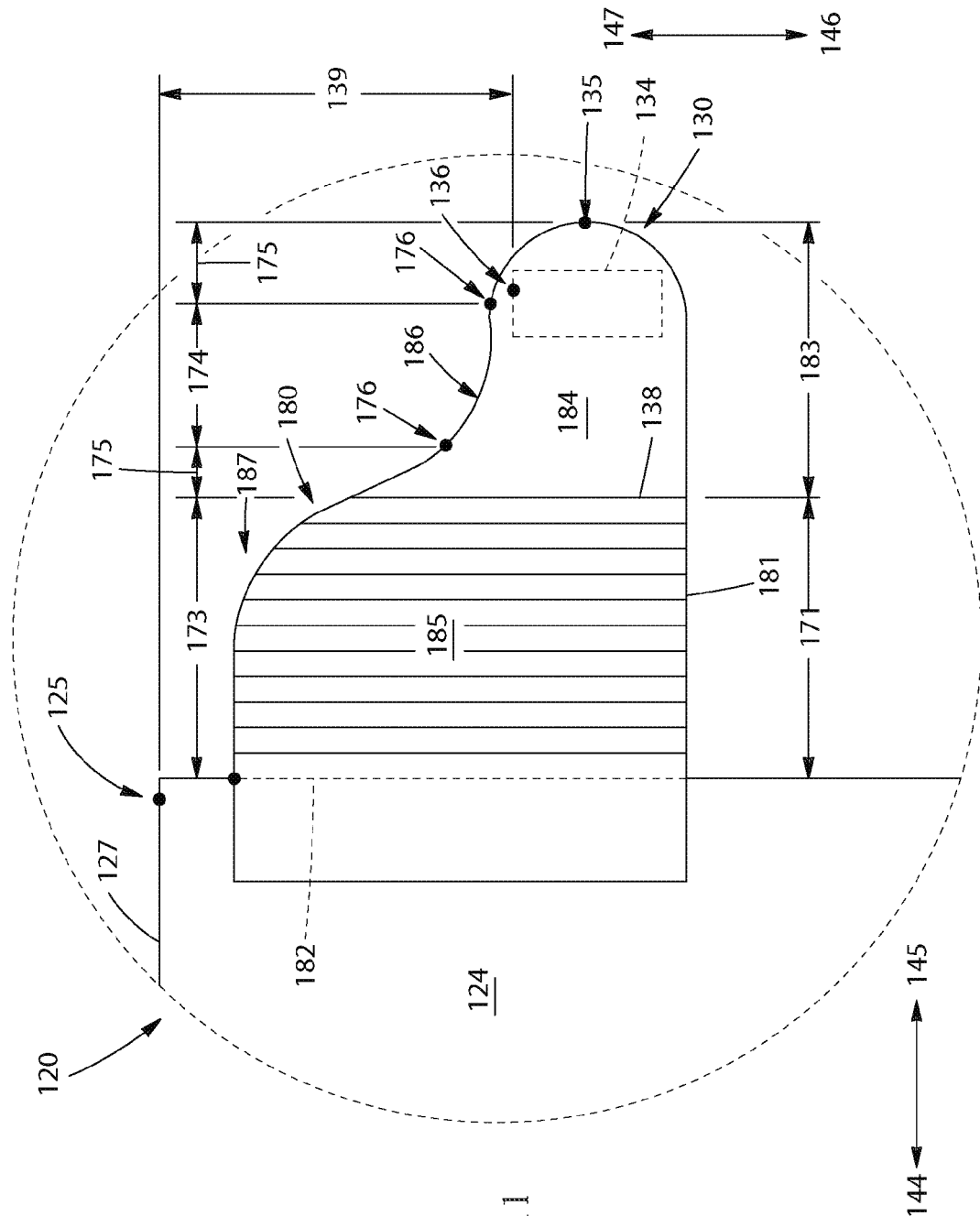
FIG. 11 illustrates an enlarged view of a portion of the first front-fastenable wearable absorbent article of FIG. 9.

The first discrete, integrally-formed side ears 130, described further in connection with FIG. 11, are shaped for the body of the first wearer 110. In particular, the first discrete, integrally formed-side ears 130 are shaped to fit high on the first sides 114 and low on the first belly 116 of the first wearer 110. Since the first discrete, integrally-formed side ears 130 fit low on the first belly 116, the first discrete, integrally-formed side ears 130 can accommodate its significant protrusion. Also, the concave upper edges of the first discrete, integrally-formed side ears 130 help cup the round underside of the protruding first belly 116 to reduce red-marking and improve comfort on the first belly 116. Since the first discrete, integrally-formed side ears 130 fit low on the first belly 116, the landing zone 123 is also disposed low on the front 122 of the diaper.

In an embodiment where the first wearer 110 is at a first or second stage of development, the first wearer 110 may have a low activity level with little to no mobility or movement, so the first discrete, integrally-formed side ears 130 do not impede the first wearer's mobility. Thus, due to the shape of the first discrete, integrally-formed side ears 130, the first article 120 provides good fit and comfort to the body of the first wearer 110.

In various embodiments, the shape of part, parts, or all of the first front waist edge 126 can match the shape of part, parts, or all of upper edges of the first side ears. The first side ears 130 have an end region with a first end region upper edge portion, wherein at least part of the first end region upper edge has a first overall contour. When the first article 120 is formed for wearing, a portion of the first front waist edge 126 that is proximate to the first end region upper edge portion can have a first waist edge overall contour that is substantially the same as the first overall contour of the first end region upper edge portion. The first article 120 can accommodate the first wearer's large, protruding belly 116 with the combination of the concave shaped upper edge and/or the concave shaped first front waist edge 126.

Figure 2:
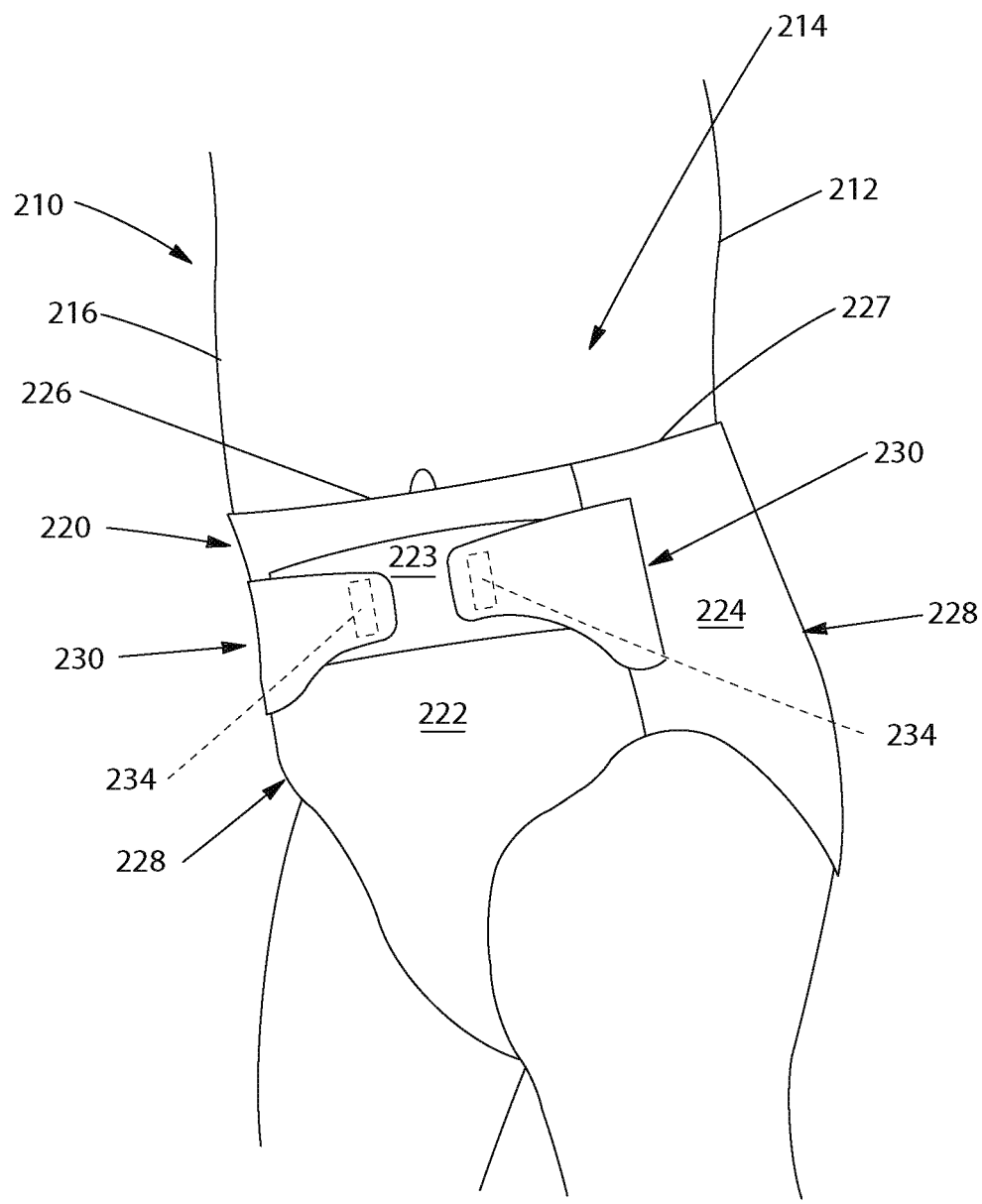
FIG. 2 illustrates a perspective view of a second front-fastenable wearable absorbent article fastened on a wearer of a second size, including discrete, integrally-formed side ears shaped to fit high on the wearer's sides and high on the belly of the second wearer, according to embodiments of the present disclosure.

FIG. 2 illustrates a perspective view of a second front-fastenable wearable absorbent article 220 fastened on a second wearer 210 of a second size, including second discrete, integrally-formed side ears 230 shaped to fit high on first sides 214 and high on a second belly 216 of the second wearer 210, according to embodiments of the present disclosure. The second article 220 is sized for the second wearer 210. The second wearer 210 may of any size greater than the size of the first wearer 110 of FIG. 1, but does not have to be the size for the next consecutive article. For example, if the first wearer 110 is of the size for an article of size one, than the second wearer 120 can be of the size for an article of size two, size three, or any greater size. In the embodiment of FIG. 2, the second wearer 210 is in a second stage of development, corresponding to a mobile baby. However, in various embodiments, the second wearer 210 may be in another stage of development. The second discrete, integrally-formed side ears 230 also have upper edges with convex portions, as described in connection with the embodiment of FIG. 12. In embodiments throughout the present disclosure, a convex portion can have a fixed radius or a variable radius over its length.

The second wearer 210 has a second navel, a second back 212, second sides 214, the second belly 216, and second legs. The second belly 216 is relatively flat, for the stature of the second wearer 216. Since the second belly 216 is relatively flat, it does not tend to protrude significantly. The second wearer 210 is larger than the first wearer 110 of FIG. 1. However, the second belly 216 protrudes proportionally less than the first belly 116 of the first wearer 110.

The second wearer 210 may wear an absorbent article that is larger than an absorbent article for the first wearer 110. For example, the second wearer 210 can wear an absorbent article of size one or larger while the first wearer 110 can wear an absorbent article that is size newborn. Also for example, the second wearer 210 can wear an absorbent article of size two while the first wearer 110 can wear an absorbent article that is size one or smaller.

The second wearer 210 may be at a stage of development that is later than a stage of development for the first wearer 110. As an example, the second wearer 210 can be at a fourth stage of development, while the first wearer 110 can be at a third or earlier stage of development. As another example, the second wearer 210 can be at a third stage of development, while the first wearer 110 can be at a second or earlier stage of development.

The second article 220 has a second front 222, a second back 224, a second chassis 228, and second discrete, integrally-formed side ears 230. The second front 222 has a second front waist edge 226. The second back 224 has a second back waist edge 227. The second discrete, integrally formed-side ears 230 are joined to the second back 224, extend around the second sides 214, and fasten to the second front 222 within a landing zone 223. The second discrete, integrally-formed side ears 230 have second attachment areas 234. In the embodiment of FIG. 2, the second discrete, integrally-formed side ears 230 are integrally-formed.

Figure 12:
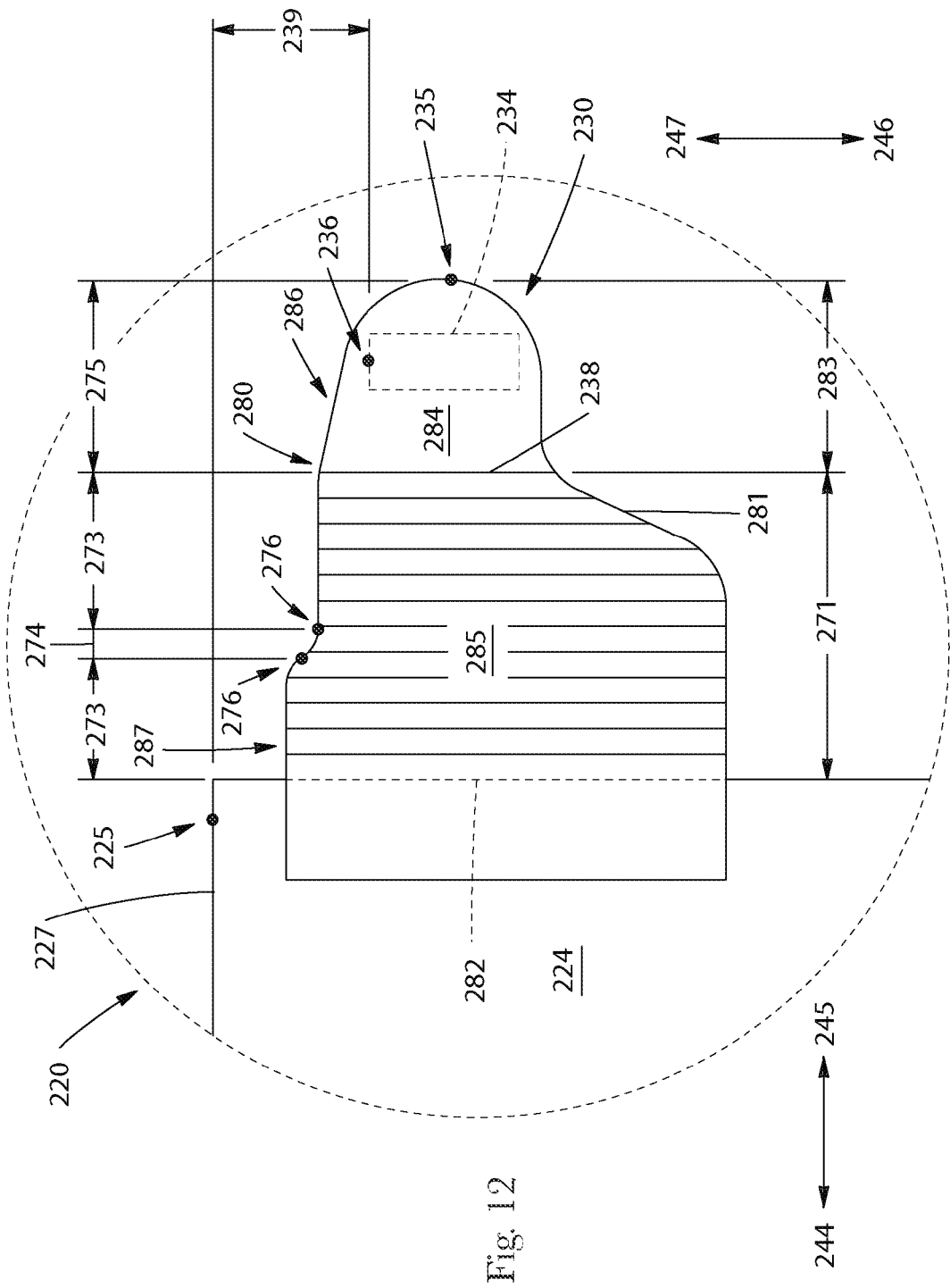
FIG. 12 illustrates an enlarged view of a portion of the second front-fastenable wearable absorbent article of FIG. 10.

The second discrete, integrally-formed side ears 230, described further in connection with FIG. 12, are shaped for the body of the second wearer 210. In particular, the second discrete, integrally-formed side ears 230 are shaped to fit high on the second sides 214 and high on the second belly 216 of the second wearer 210. Since the second discrete, integrally-formed side ears 230 fit high on the second belly 216, the landing zone 223 is also disposed high on the second front 222 of the second article 220.

In an embodiment where the second wearer 210 is at a third or fourth stage of development, the second wearer 210 may have a moderate to high activity level with various forms of mobility. Since the second discrete, integrally-formed side ears 230 fit high on the second belly 216, the second discrete, integrally-formed side ears 230 fit snugly on the second wearer's flatter second belly 216. Also, since the second discrete, integrally-formed side ears 230 fit high on the second belly 216, the second discrete, integrally-formed side ears 230 are spaced away from the second legs, so the second article 220 can accommodate the second wearer's significant associated leg movement. Thus, due to the shape of the second discrete, integrally-formed side ears 230, the second article 220 provides good fit and comfort to the body of the second wearer 210.

In various embodiments, the shape of part, parts, or all of the second front waist edge 226 can match the shape of part, parts, or all of upper edges of the second side ears 230. The second side ears 230 have an end region with a second end region upper edge portion, wherein at least part of the second end region upper edge portion has a second overall contour. When the second article 220 is formed for wearing, a portion of the second front waist edge 226 that is proximate to the second end region upper edge can have a second waist edge overall contour that is substantially the same as the second overall contour of the second end region upper edge.

A first article and a second article can form part or all of an array of front-fastenable wearable absorbent articles capable of meeting the needs of wearers of different shapes and activity levels. In various embodiments, the first article can be the article 120 of FIG. 1, the article 520 of FIG. 5, or the article 720 of FIG. 7, and the second article can be the article 220 of FIG. 2, the article 620 of FIG. 6, or the article 820 of FIG. 8, including any variations of these articles described herein. In an embodiment of the present disclosure, the array can include two, three, four, five, six, seven, or more front-fastenable wearable absorbent articles with differing ear shapes corresponding to various body shapes and activity levels for particular wearers. As an example, an array may have front-fastenable wearable absorbent articles with different ear shapes for each of three or four stages of development of a wearer. As another example, an array may have front-fastenable wearable absorbent articles with a different ear shape for each size of article in the array.

An array having more than two articles can be configured in various ways. As a first example, the shape of the side ears can progress from a minimum concave dimension to a minimum convex dimension, from the smallest article in the array to the largest article in the array. In a second example, two or more consecutively sized articles in the array may have the same side ear shape (same concave dimensions and/or convex dimensions), while one or more other articles in the array have differing ear shapes, as described herein.

FIG. 3 illustrates a side view of the first wearer 110 and the first front-fastenable wearable absorbent article 120 of FIG. 1.

FIG. 4 illustrates a side view of the second wearer 210 and the second front-fastenable wearable absorbent article 220 of FIG. 2.

FIG. 5 illustrates a first front-fastenable wearable absorbent article 520 fastened on a first wearer 510. The first wearer 510 is the first wearer 110 of FIG. 1. The elements of the first article 520 are configured in the same way as the like-numbered elements in FIG. 1, except as subsequently described. Throughout the present disclosure, the term "like-numbered" is intended to illustrate a correspondence between labels of elements wherein the last two numbers in the labels of the elements are the same. Element labels are considered to be like-numbered despite different numeral prefixes corresponding to figure numbers. The first front-fastenable wearable absorbent article 520 includes first discrete, tape-tab side ears 532 having first tape tabs 533 with first attachment areas. The first discrete, tape-tab side ears 532 are joined to the first back 524, extend around the first sides 514, and fasten to the first front 522. Similar to the first discrete, integrally-formed side ears 130, the first discrete, tape-tab side ears 532 are configured to fit high on the first sides 514 and low on the first belly 516, to provide good fit and comfort to the body of the first wearer 510.

FIG. 6 illustrates a second front-fastenable wearable absorbent article 620 fastened on a second wearer 610. The second wearer 610 is the second wearer 210 of FIG. 2. The elements of the second article 620 are configured in the same way as the like-numbered elements in FIG. 2, except as subsequently described. The second front-fastenable wearable absorbent article 620 includes second discrete, tape-tab side ears 632 having second tape tabs 633 with second attachment areas.

The second discrete, tape-tab side ears 632 are joined to the second back 624, extend around the second sides 614, and fasten to the second front 622. Similar to the second discrete, integrally-formed side ears 230, the second discrete, tape-tab side ears 632 are configured to fit high on the second sides 614 and high on the second belly 616, to provide good fit and comfort to the body of the second wearer 610.

FIG. 7 illustrates a first front-fastenable wearable absorbent article 720 fastened on a first wearer 710. The first wearer 710 is the first wearer 110 of FIG. 1. The elements of the first article 710 are configured in the same way as the like-numbered elements in FIG. 1, except as subsequently described. The first front-fastenable wearable absorbent article 720 includes a first chassis 729 with first unitary, integrally-formed side ears 731 with first attachment areas. As used herein, the term "unitary," with respect to side ears, refers to side ears that are not discrete components added to the chassis, but rather, may be formed from an extension of at least one chassis component, such as a backsheet, a topsheet, a cuff material, or any other chassis or core component. The first unitary, integrally-formed side ears 731 extend from the first back 724, around the first sides 714, and fasten to the first front 722. Similar to the first discrete, integrally-formed side ears 130, the first unitary, integrally-formed side ears 731 have a concave-shaped upper edge such that the first unitary, integrally-formed side ears 731 fit high on the first sides 714 and low on the first belly 716 to provide good fit and comfort to the body of the first wearer 710.

FIG. 8 illustrates a second front-fastenable wearable absorbent article 820 fastened on a second wearer 810. The second wearer 810 is the second wearer 210 of FIG. 2. The elements of the second article 810 are configured in the same way as the like-numbered elements in FIG. 2, except as subsequently described. The second front-fastenable wearable absorbent article 820 includes a second chassis 829 with second unitary, integrally-formed side ears 831 with second attachment areas. The second unitary, integrally-formed side ears 831 extend from the second back 824, around the second sides 814, and fasten to the second front 822. Similar to the second discrete, integrally-formed side ears 130, the second unitary, integrally-formed side ears 831 have a convex-shaped upper edge such that the second unitary, integrally-formed side ears 831 fit high on the second sides 814 and high on the second belly 816 to provide good fit and comfort to the body of the second wearer 810.

Figure 9:
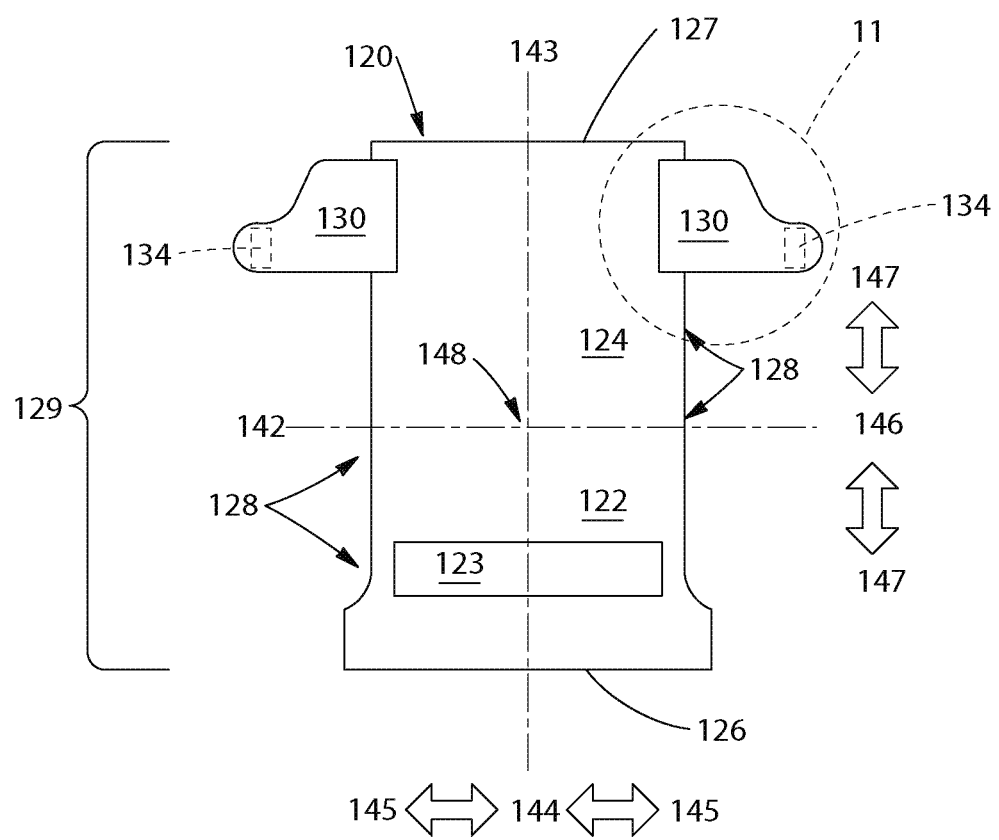
FIG. 9 illustrates a plan view of the outside of the first front-fastenable wearable absorbent article of FIG. 1 laid out flat.

FIG. 9 illustrates a plan view of the outside of the first front-fastenable disposable wearable absorbent article 120 of FIG. 1 laid out flat. A longitudinal centerline 143 and a lateral centerline 142 provide lines of reference for referring to relative locations of the front-fastenable disposable wearable absorbent article 120. The longitudinal centerline 143 runs between the waist edges and separates the first absorbent article 120 into left and right halves. The lateral centerline 142 is perpendicular to the longitudinal centerline 143 and separates the front 122 from the back 124. When a first location is nearer to the longitudinal centerline 143 than a second location, the first location can be considered laterally inboard 144 to the second location. Similarly, the second location can be considered laterally outboard 145 from the first location. When a third location is nearer to the lateral centerline 142 than a fourth location, the third location can be considered longitudinally inboard 146 to the fourth location. Also, the fourth location can be considered longitudinally outboard 147 from the third location. The longitudinal centerline 143 and the lateral centerline 142 cross at a center 148 of the wearable absorbent article 120.

FIG. 9 includes arrows indicating relative directions for laterally outboard 145, laterally inboard 144, longitudinally outboard 147, and longitudinally inboard 146, each with respect to the wearable absorbent article 120. Throughout the present disclosure, a reference to a length or a longitudinal dimension, measurement, line, or direction refers to a dimension, measurement, line, or direction that is substantially or completely parallel to the longitudinal centerline 143 and a reference to a width or a lateral dimension, measurement, line, or direction refers to a dimension, measurement, line, or direction that is substantially or completely parallel to the lateral centerline 142. The terminology for describing relative locations, as discussed above, is used for wearable absorbent articles throughout the present disclosure, as will be understood by one of ordinary skill in the art. The first chassis 128 has a first overall longitudinal chassis length 129 extending from the first front waist edge 126 to the first back waist edge 127.

Figure 10:
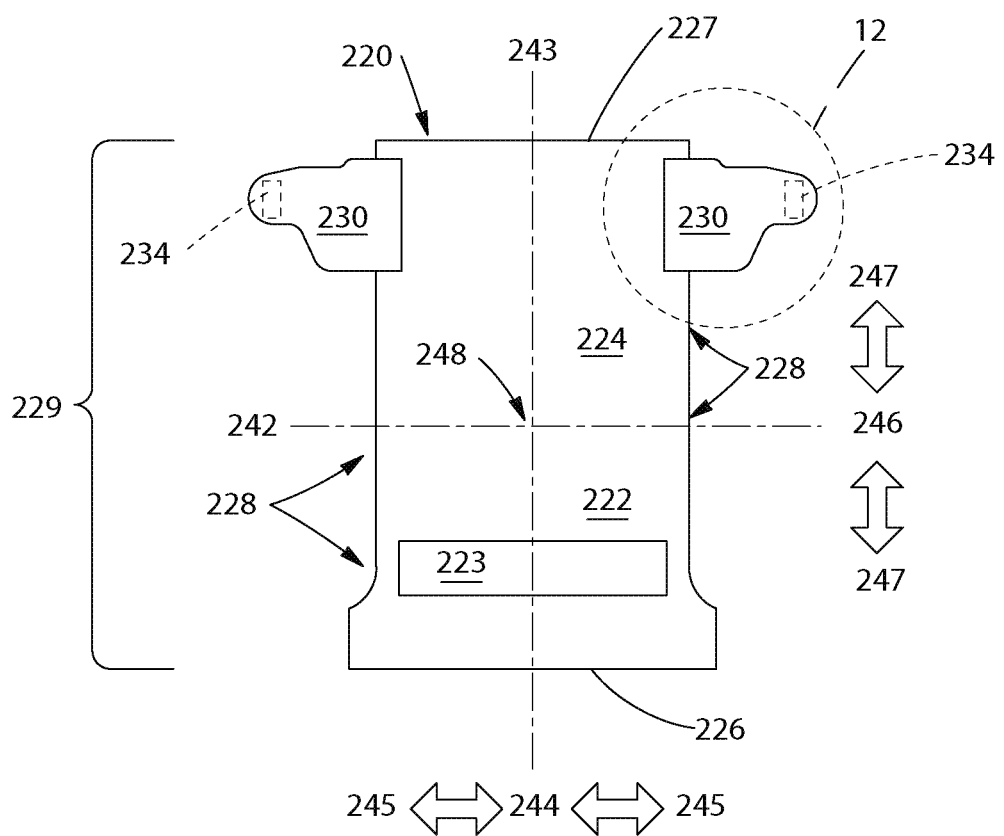
FIG. 10 illustrates a plan view of the outside of the second front-fastenable wearable absorbent article of FIG. 2 laid out flat.

FIG. 10 illustrates a plan view of the outside of the second front-fastenable wearable absorbent article 220 of FIG. 2 laid out flat. A longitudinal centerline 243 and a lateral centerline 242 provide lines of reference that cross at a center 248 of the wearable absorbent article 220. FIG. 10 also includes arrows indicating relative directions for laterally outboard 245, laterally inboard 244, longitudinally outboard 247, and longitudinally inboard 246, each with respect to the second wearable absorbent article 220. The second chassis 228 has a second overall longitudinal chassis length 229 extending from the second front waist edge 226 to the second back waist edge 227.

FIG. 11 illustrates an enlarged view of a portion of the first front-fastenable wearable absorbent article 120 of FIG. 9. The first discrete, integrally-formed side ear 130 is a separate component that is joined to the first back 124 at a first junction line 182. The first discrete, integrally-formed side ear 130 has a first upper edge 180, a first lower edge 181, a first laterally extensible region 185, a first end region 184, and a first farthest laterally outboard endpoint 135.

In various embodiments, the first laterally extensible region 185 is laterally extensible. As used herein, the term "laterally extensible" refers to characteristics of a material that has the ability to extend in the lateral direction beyond its relaxed length to an extended length of at least 110% but less than 250% of its original relaxed length without a rupture or breakage that renders the material unusable for its intended purpose. However, in various embodiments, a laterally extensible material may be able to extend to an extended length of at least 120%, at least 130%, at least 140%, or at least 150% of its original relaxed length, but less than 250%, less than 225%, or less than 200%, or combinations of any of these values, or ranges formed from any of these values. A material that does not meet this definition is considered laterally inextensible. The first laterally extensible region 185 may be elastically laterally extensible. As used herein "elastically laterally extensible" refers to characteristics of laterally extensible materials that have the ability to return to approximately their original dimensions after a lateral force that extended the extensible material is removed. In some embodiments, the first laterally extensible region 185 may be laterally extensible but not elastically laterally extensible. For example, the first laterally extensible region 185 may lack the ability to return to approximately its original dimensions after a force that extended the extensible region is removed.

The first laterally extensible region 185 extends from the first junction line 182 to a first laterally outboard extensible region edge 138 and from a portion of the first upper edge 180 to a portion of the first lower edge 181. The term "junction line" has a different meaning for different style side ears. For a discrete side ear or for a unitary side ear with a chassis that is not laterally extensible, the term "junction line" means a longitudinal line that passes through the farthest laterally inboard point at which the side ear or a portion thereof is laterally extensible. For a unitary side ear with a laterally extensible chassis, the term "junction line" refers to a longitudinal line that passes through the chassis at its narrowest width on the side from which the unitary side ear extends.

The first laterally outboard extensible region edge 138 is located at the farthest laterally outboard point at which the side ear or a portion thereof is laterally extensible. The first upper edge 180 has a first extensible region upper edge portion 187 that extends from the first junction line 182 to the first farthest laterally outboard extensible region edge 138. The intersection between the first upper edge 180 and the first junction line 182 marks the inboard endpoint of the first upper edge 180. The first extensible region upper edge portion 187 has a first extensible region upper edge overall lateral dimension 171 measured laterally from the first junction line 182 to the first laterally outboard extensible region edge 138.

The first end region 184 extends from the first laterally outboard extensible region edge 138 to the first farthest laterally outboard endpoint 135 and from a portion of the first upper edge 180 to a portion of the first lower edge 181. The first farthest laterally outboard endpoint 135 is the farthest laterally outboard point on the first side ear 130. The first farthest laterally outboard endpoint 135 is the outboard endpoint of the first upper edge 180. The first upper edge 180 has a first end region upper edge portion 186 that extends from the first laterally outboard extensible region edge 138 to the first farthest laterally outboard endpoint 135. The first end region 184 has a first end region upper edge overall lateral dimension 183 measured laterally from the first laterally outboard extensible region edge 138 to the first farthest laterally outboard endpoint 135.

An upper edge of a side ear can have one or more concave portions and/or one or more convex portions. A portion is considered concave or convex using the Test Method for Determining Concave and Convex Portions, described below. As used herein, a first total concave lateral dimension is the sum of all of the first lateral dimensions of all of the concave portions for a designated portion of the first upper edge 180. Similarly, a first total convex lateral dimension is the sum of all of the first lateral dimensions of all of the convex portions for a designated portion of the first upper edge 180. Total concave lateral dimensions and the total convex lateral dimensions can be calculated using the Test Method for Determining Concave and Convex Dimensions and Percentages described below.

In the embodiment of FIG. 11, the first extensible region upper edge portion 187 has no concave portions and one first extensible region convex portion 173. So, the first extensible region upper edge portion 187 has a first total concave lateral dimension of zero and a first total convex lateral dimension, which is equal to the lateral dimension of the first extensible region convex portion 173. In various embodiments, the first extensible region upper edge portion 187 can have a first total concave lateral dimension that is at least 25%, at least 50%, or at least 75% of the first extensible region upper edge overall lateral dimension 171, or any integer value of percentage between these values, or any range of values based on any of these numbers.

The first end region upper edge portion 186 has one first end region concave portion 174 and two first end region convex portions 175, separated by inflection points 176. So, the first end region upper edge portion 186 has a first total concave lateral dimension, which is the lateral dimension of the first end region concave portion 174 and a first total convex dimension, which is the sum of the lateral dimensions of the two first end region convex portions 175. In various embodiments, the first end region upper edge portion 186 can have a first total concave lateral dimension that is at least 25%, at least 50%, or at least 75% of the first end region upper edge overall lateral dimension 183, or any integer value of percentage between these values, or any range of values based on any of these numbers.

In various embodiments, the first end region upper edge portion 186 can have a single continuous concave portion with an overall lateral dimension that is at least 25%, at least 50%, or at least 75% of the first end region upper edge overall lateral dimension 183, or any integer value of percentage between these values, or any range of values based on any of these numbers. Also, in various embodiments, the first end region upper edge portion 186 can have a first total convex lateral dimension that is less than 50% or less than 25% of the first end region upper edge overall lateral dimension 183, or any integer value of percentage between these values, or any range of values based on any of these numbers.

In various embodiments of the present disclosure, the first end region upper edge portion 186 only has slopes that are negative or zero, such that, from its inboard endpoint to its outboard endpoint, the first end region upper edge portion 186 does not curve back up towards the first wearer's belly. As used herein, the term "slope" refers to the rate of change between two points on the upper edge of the side ear expressed as the difference in longitudinal location between the two points divided by the difference in lateral location between the two points. For the purpose of determining slope, FIG. 11 is considered to be located in the first quadrant of a Cartesian coordinate system, where the laterally outboard direction 145 is the positive X direction and the longitudinally outboard direction 147 is the positive Y direction.

The first discrete, integrally-formed side ears 130 are shaped to fit high on the first sides and low on the first belly of the first wearer. Since the first discrete, integrally-formed side ears 130 fit low on the first belly, the first discrete, integrally-formed side ears 130 can accommodate its significant protrusion. Also, the concave upper edges of the first discrete, integrally-formed side ears 130 help cup the round underside of the protruding first belly to reduce red-marking and improve comfort on the first belly.

The first side ear 130 has a first attachment area 134 with a first farthest longitudinally outboard attachment area point 126. The location of the first side ear attachment area 134 affects the fit on the first wearer's belly. The longitudinal location of the first attachment area 134, when scaled by the overall longitudinal chassis length 129 of FIG. 9, positions the attachment area 134 low in relationship to the front waist edge of the first article.

The first article 120 has a first back waist edge 127 with a first farthest longitudinally inboard back waist edge point 125, which is the farthest longitudinally inboard point on the first back waist edge 127. A first chassis edge to attachment edge distance 139 is measured from the first farthest longitudinally inboard back waist edge point 125 to the first farthest longitudinally outboard attachment area point 136. In various embodiments, the first chassis edge to attachment edge distance 139 may be in the range of 10-50 millimeters, or 15-45 millimeters, or 20-40 millimeters, or any integer value between these values, or any range of values based on any of these numbers. A first chassis edge to attachment edge percentage is the first chassis edge to attachment edge distance 139 expressed as a percentage of the first overall longitudinal chassis length 129 of FIG. 9. In various embodiments, the first chassis edge to attachment edge percentage may be at least 6%, at least 8%, or at least 10% of the first overall longitudinal chassis length 129, or any integer value of percentage between these values or greater than these values (up to 25%), or any range of values based on any of these numbers.

FIG. 12 illustrates an enlarged view of a portion of the second front-fastenable wearable absorbent article 220 of FIG. 10. The second discrete, integrally-formed side ear 230 is a separate component that is joined to the second back 224 at a second junction line 282. The second side ear 230 has a second upper edge 280, a second lower edge 281, a second laterally extensible region 285, and a second end region 284.

In various embodiments, the second laterally extensible region 285 is laterally extensible. The second laterally extensible region 285 may be elastically laterally extensible. In various embodiments, the second laterally extensible region 285 may be laterally extensible but not elastically laterally extensible.

The second laterally extensible region 285 extends from the second junction line 282 to a second laterally outboard edge 238 and from a portion of the second upper edge 280 to a portion of the second lower edge 281. The second laterally outboard extensible region edge 238 is located at the farthest laterally outboard point at which the side ear or a portion thereof is laterally extensible. The second upper edge 280 has a second extensible region upper edge portion 287 that extends from the second junction line 282 to the second farthest laterally outboard extensible region edge 238. The second extensible region upper edge portion 287 has a second extensible region upper edge overall lateral dimension 271 measured laterally from the second junction line 282 to the second laterally outboard extensible region edge 238.

The second end region 284 extends from the second laterally outboard extensible region edge 238 to the second farthest laterally outboard endpoint 235 and from a portion of the second upper edge 280 to a portion of the second lower edge 281. The second farthest laterally outboard endpoint 235 is the farthest laterally outboard point on the second side ear 230. The second upper edge 280 has a second end region upper edge portion 286 that extends from the second laterally outboard extensible region edge 238 to the second farthest laterally outboard endpoint 235. The second end region 284 has a second end region upper edge overall lateral dimension 283 measured laterally from the second laterally outboard extensible region edge 238 to the second farthest laterally outboard endpoint 235.

In the embodiment of FIG. 12, the second extensible region upper edge portion 287 has one second extensible region concave portion 274 and two second extensible region convex portions 273, separated by second inflection points 276. So, the second extensible region upper edge portion 287 has a second total concave lateral dimension, which is the lateral dimension of the second extensible region concave portion 274, and a second total convex lateral dimension, which is the sum of the lateral dimensions of the two second extensible region convex portions 273. In various embodiments of the present disclosure, the second extensible region upper edge portion 287 can have a second total convex lateral dimension that is at least 25%, at least 50%, or at least 75% of the second extensible region upper edge overall lateral dimension 271, or any integer value of percentage between these values, or any range of values based on any of these numbers.

The second end region upper edge portion 286 has zero concave portions and one first end region convex portion 275. So, the second end region upper edge portion 286 has a second total concave lateral dimension of zero, and a second total convex dimension, which is the lateral dimension of the second end region convex portion 275. In various embodiments, the second extensible region upper edge portion 287 can have a second total convex lateral dimension that is at least 25%, at least 50%, or at least 75% of the second end region upper edge overall lateral dimension 283, or any integer value of percentage between these values, or any range of values based on any of these numbers.

In various embodiments, the second end region upper edge portion 286 can have a single continuous convex portion that is at least 25%, at least 50%, or at least 75% of the second end region upper edge overall lateral dimension 283, or any integer of percentage between these values, or any range of values based on any of these numbers. Also, in various embodiments, the second end region upper edge portion 286 can have a total concave lateral dimension that is less than 50% or less than 25% of the second end region upper edge overall lateral dimension 283, or any integer value of percentage between these values, or any range of values based on any of these numbers.

The second discrete, integrally-formed side ears 230 are shaped to fit high on the second sides 214 and high on the second belly 216 of the second wearer 210. Since the second discrete, integrally-formed side ears 230 fit high on the second belly 216, the second discrete, integrally-formed side ears 230 can accommodate the belly's minimal protrusion. Also, the convex upper edges of the second discrete, integrally-formed side ears 230 help support the second article 220 on the second wearer 210.

As described above, a first article and a second article can form part or all of an array of front-fastenable wearable absorbent articles. In various embodiments, the array may comprise a third front-fastenable wearable absorbent article, along with the first article and the second article. The third article may be sized for a wearer of a larger size than the first wearer and for a smaller size than the second wearer. The third article may have a third side ear shaped for the third wearer size. The third side ear may have a third side ear end region upper edge portion and a third end region upper edge overall lateral dimension. The third end region upper edge portion may have at least one concave portion forming a third total concave lateral dimension that is less than 50% of the third end region upper edge overall lateral dimension, or any integer value of percentage less than 50%. The third end region upper edge portion may also have at least one convex portion forming a third total convex lateral dimension that is less than 50% of the third end region upper edge overall lateral dimension, or any integer value of percentage less than 50%.

The second side ear 230 has a second attachment area 234 with a second farthest longitudinally outboard attachment area point 236. The longitudinal location of the second attachment area 234, when scaled by the overall longitudinal chassis length 229 of FIG. 10, is smaller than the longitudinal location of the first attachment area 134 of FIG. 1. The second article 220 has a second back waist edge 227 with a second farthest longitudinally inboard back waist edge point 225, which is the farthest longitudinally inboard point on the second back waist edge 227. A second chassis edge to attachment edge distance 239 is measured from the second farthest longitudinally inboard back waist edge point 225 to the second farthest longitudinally outboard attachment area point 236. In various embodiments, the second chassis edge to attachment edge distance 239 may be in the range of 25-75 millimeters, or 30-60 millimeters, or 35-55 millimeters, or any integer value between these values, or any range of values based on any of these numbers. A second chassis edge to attachment edge percentage is the second chassis edge to attachment edge distance 239 expressed as a percentage of the second overall longitudinal chassis length 229. In various embodiments, the second chassis edge to attachment edge percentage may be at most 7%, at most 9%, or at most 11% of the second overall longitudinal chassis length 229, or any integer value of percentage between these values or less than these values (down to 0%), or any range of values based on any of these numbers.

In various embodiments, an array has a first article and second article wherein the first chassis edge to attachment edge percentage is greater than the second chassis edge to attachment edge percentage. A greater first chassis edge to attachment edge distance 139 from FIG. 11 positions the first attachment area low on the belly of the first wearer in order to cup the belly of the first wearer. A lesser second chassis edge to attachment edge distance 239 from FIG. 12 positions the second attachment area high on the belly of the second wearer in order to support the second article on the second wearer and provide free movement of the second wearer's legs. In an embodiment of the present disclosure, the first chassis edge to attachment edge percentage is at least 1 percentage point greater, at least 2 percentage points greater, or at least 3 percentage points greater than the second chassis edge to attachment edge percentage, or any integer value of percentage greater than these values (up to 10 percentage points), or any range of values based on any of these numbers.

A difference in percentage points refers to a difference between the numerical value of one percentage and the numerical value of another percentage. The difference can be determined by subtracting one value from the other. For example, an array has a first article and a second article. The first article has a first chassis edge to attachment edge percentage of 11%. The second article has a second chassis edge to attachment edge percentage 6%. In this example, the first chassis edge to attachment edge percentage is considered to be 5 percentage points greater than the second chassis edge to attachment edge percentage. This is the meaning of percentage points throughout the present disclosure.

An array having more than two articles can be configured in various ways. As a first example, for consecutively-sized articles in the array, one chassis edge to attachment edge percentage can be at least 0 percentage points, at least 1 percentage point, or at least 2 percentage points greater than or less than the other chassis edge to attachment edge percentage, or any integer value of percentage greater than these values (up to 10 percentage points), or any range of values based on any of these numbers. As a second example, the smallest article in the array and the largest article in the array may have a difference in chassis edge to attachment edge percentage of at least 1 percentage point, at least 2 percentage points, or at least 3 percentage points, or any integer value of percentage greater than these values (up to 10 percentage points), or any range of values based on any of these numbers. In a third example, the chassis edge to attachment edge percentage may stay the same from one size to the next size, or may decrease from one size to the next size, such that the chassis edge to attachment edge percentage never increases from an article of a smaller size to an article of a larger size.

Figure 13:
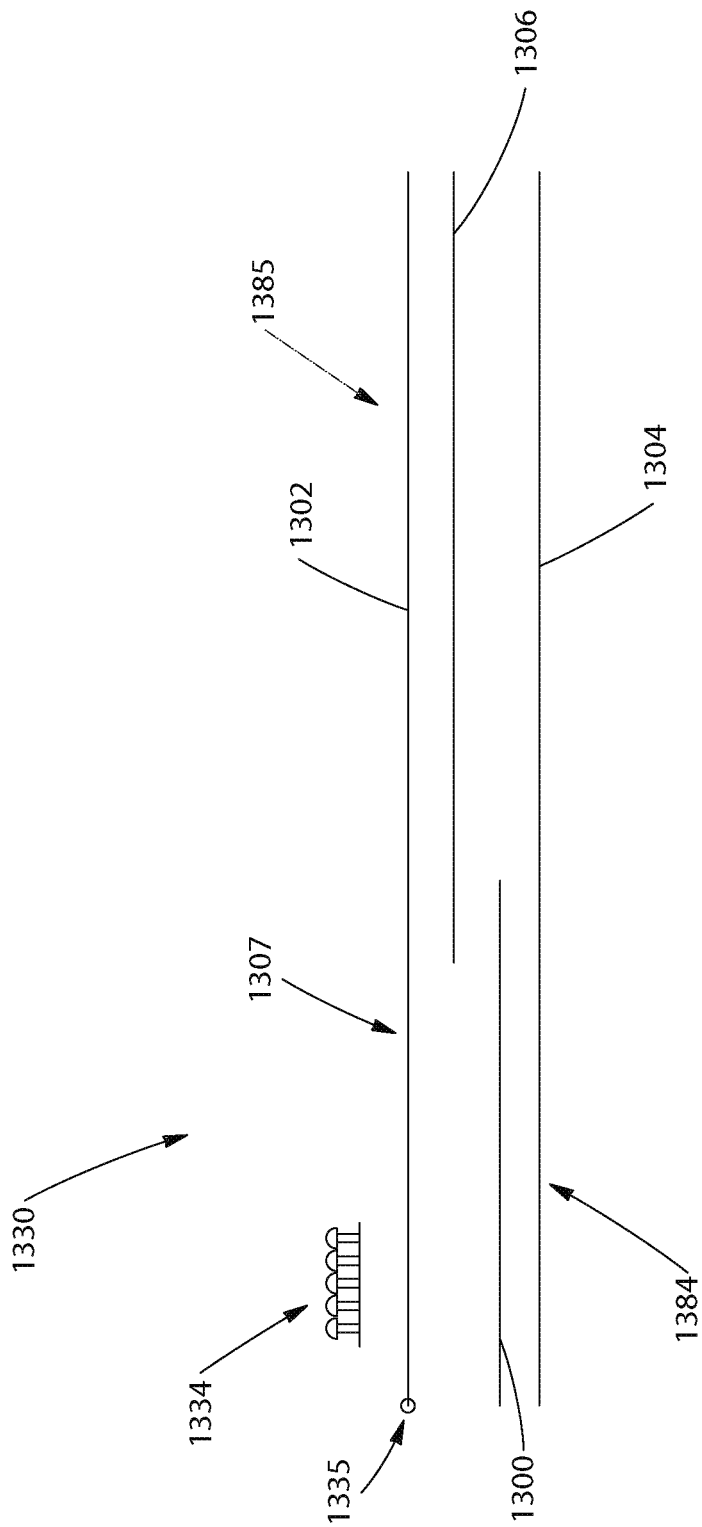
FIG. 13 illustrates an exploded cross-sectional view of a side ear, according to embodiments of the present disclosure.

FIG. 13 illustrates an exploded cross-sectional view of an exemplary side ear 1330, separate from a disposable wearable absorbent article. The process of making a side ear is described in more detail in US patent application, Pub. No. 2007/0157441, which is incorporated herein by reference. A laterally extensible region 1385 may comprise a first substrate 1302, a second substrate 1304, and an elastomeric element 1306. The elastomeric element 1306 can be sandwiched between the first substrate 1302 and the second substrate 1304. Although not shown, the elastomeric element 1306 can be joined to the first substrate 1302 and/or the second substrate 1304 by a first bonding agent, a second bonding agent, and/or any other suitable means.

As shown in FIG. 13, in some embodiments, a stiffening material 1300 can be disposed between the first substrate 1302 and the second substrate 1304 to increase the stiffness of an end region 1384. In other embodiments, the stiffening material 1300 can be disposed between the elastomeric element 1306 and the second substrate 1304. In embodiments where the stiffening material 1300 overlaps a portion of the elastomeric element 1306, a bonding agent can be disposed between the stiffening material 1300 and the elastomeric element 1306.

Additionally, as shown, in some embodiments, the elastomeric element 1306 can extend from the laterally extensible region 1385 to the end region 1384 such that only a portion of the end region 1384, e.g. an intermediate zone 1307, comprises a portion of the elastomeric element 1306. In other embodiments, the elastomeric element 1306 can extend from the laterally extensible region 1385 to a farthest laterally outboard endpoint 1335 such that the elastomeric element 1306 comprises the entire end region 1384. In other embodiments, the elastomeric element 1306 can extend from the laterally extensible region 1385 to the end region 1384 such that the intermediate zone 1307 and the attachment area 1334 each comprise a portion of the elastomeric element 1306.

The side ears of the present invention may comprise a wide variety of materials. For example, the first substrate 1302 and/or the second substrate 1304 may comprise a woven, nonwoven, film, a laminate, the like, or any combination thereof. In some embodiments, the first substrate 1302 and/or the second substrate 1304 may be laterally extensible and/or elastically extensible. Where the first substrate 1302 and/or the second substrate 1304 comprise a nonwoven, any suitable nonwoven can be used. In some embodiments, the nonwoven may comprise one layer of fibers. In other embodiments, the nonwoven may comprise more than one layer of fibers. Any suitable nonwoven can be used. For example, a suitable nonwoven may comprise fibers made of polypropylene, polyethylene, polyester, nylon, cellulose, polyamide, or combinations of such materials. Fibers of one material or fibers of different materials or material combinations may be used in the first and/or second nonwoven. Exemplary nonwoven materials include spunbond, spunbond meltblown spunbond (SMS), spunbond meltblown meltblown spunbond (SMMS), carded, meltblown, and the like. Particularly acceptable nonwovens include high elongation carded (HEC) nonwovens and deep activation polypropylene (DAPP) nonwovens. Any process known in the art may be used to make the nonwovens.

The nonwoven may comprise fibers that are bonded mechanically, including fibers that are needle punched or hydro entangled. Other suitable bonding processes for producing a suitable nonwoven for use in the present invention are spun bonding, thermally bonding, bonding by various types of chemical bonding such as latex bonding, powder bonding, and the like.

In certain embodiments, the basis weight of the nonwoven can be in the range of about 10 gsm to about 100 gsm or any individual number within the range. In other embodiments, the basis weight of the nonwoven can be in a range of about 40 gsm to about 80 gsm. In yet other embodiments, the basis weight of the nonwoven can be in a range of about 50 gsm to about 60 gsm. The basis weights of the substrates of the present invention can be any suitable basis weight.

The fibers may be of any suitable size and shape. In some embodiments, the fiber may have a denier ranging from about 1 to about 10 or any individual number within the range. In some embodiments, the denier of the fibers can range from about 1 to about 8. In other embodiments, the denier of the fibers can range from about 1 to about 5.

The elastomeric element 1306 may comprise any suitable elastic known in the art. Suitable elastomeric elements may comprise a wide variety of materials as are well known in the art. Some examples include elastomeric films, polyurethane films, elastomeric foams, formed elastic scrim and synthetic elastomers (e.g., Lycra™). A suitable elastomeric element 1306 for use in conjunction with the present invention may comprise elastic strands and/or elastic films. Any suitable elastic film known in the art can be used. Suitable elastic films may comprise polypropylene, polyethylene, polyolefins, styrene-isoprene-styrene, styrene-butadiene-styrene, or combinations thereof. The basis weight of the films can range from about 10 gsm to about 100 gsm.

Alternatively, or in conjunction with the elastic film, the elastomeric element 1306 may further comprise elastic strands. Suitable elastic strands can be made of a resilient elastic thermoplastic material. The elastic strands may be made from liquid elastic that is extruded through a die to achieve the desired strand elastic diameter and/or shape. The shape of the extruded elastic strands is not limited. For example, typical elastic strands have a circular cross sectional shape, but sometimes the elastic strands may have different shapes, such as a trilobal shape, or a flat (i.e., "ribbon" like) shape. Suitable elastic strand shapes include rectangles, circles, ellipses, diamonds, triangles, parallelograms, trapezoids, wedges, or other sections of circles or ellipses, other polygons, or other irregular enclosed shapes. Furthermore, the thickness or diameter of the elastic strands may vary in order to accommodate a particular application. Typically, the thickness of elastic strands may be in the range of about 0.02 mm to about 1 mm and the basis weight is in the range of about 20 gsm to about 300 gsm. The elastic strands may be applied separately to the substrate, can be extruded onto the substrate, or can be printed onto the substrate.

Suitable apparatuses and methods for printing elastomeric elements in any orientation are described in U.S. Application Publication No. 2004/0181200; U.S. Application Publication No. 2004/0193133; and WO 2005/110731 A3. For the printing of elastic strands, the individual elastic strands may be configured as lines or strands generally having widths less than about 2 mm and typically less than about 1 mm. Linear elastic strands may be configured as bands generally having widths between about 2 mm and about 20 mm and aspect ratios ranging from about 2:1 to about 100:1. Typically, the thickness of an elastic strand may be in the range of about 0.02 mm to about 5 mm and the basis weight is in the range of about 20 g/m$^2$ to about 300 g/m$^2$.

The first bonding agent, the second bonding agent, and/or a third bonding agent, may comprise any suitable bonding agent known in the art. For example, in some embodiments, at least one of the bonding agents may comprise an adhesive. Any suitable adhesive can be used in the present invention. For example, the adhesive may comprise styrene-olefin-styrene triblock copolymers such as styrene-isoprene-styrene, styrene-butadiene-styrene, the like, or combinations thereof.

An example of a suitable bonding agent for joining the attachment area 1334 to the stiffening material 1300 and/or the second substrate 1304 is an adhesive made from Bostik located in Wauwatosa, Wis., having a model number H2988-F02. In some embodiments, the attachment area 1334 can be joined to the stiffening material 1300 and/or the second substrate 1304 via the bonding agent plus mechanical bonds, fusion bonds, the like, or any combination thereof. In some embodiments, the attachment area 1334 can be joined to the stiffening material 1300 and/or the second substrate 1304 via mechanical bonds, fusion bonds, or the like, or any suitable combination thereof.

In some embodiments, at least one of the bonding agents may comprise a polymer. Any suitable polymer known in the art can be utilized. Some examples of suitable polymers include a high modulus hot melt polymer, or may include a molten polymer. Any suitable molten polymer can be used. Some examples of molten polymers include polyethylene, polypropylene, the like, or any suitable combinations thereof.

In some embodiments, the basis weight of the first bonding agent, the second bonding agent, and/or the third bonding agent in the attachment area 1334 can be greater than or equal to about 30 gsm. In other embodiments, the first bonding agent, the second bonding agent, and/or the third bonding agent in the attachment area 1334 can have a basis weight of greater than or equal to about 60 gsm. In some embodiments, first bonding agent, the second bonding agent, and/or the third bonding agent in the attachment area 1334 can have a basis weight of greater than or equal to about 100 gsm.

The stiffening material 1300 can be any suitable stiffening material known in the art. Some examples of suitable stiffening materials 1300 include webs of any type, e.g. woven, nonwoven, laminates, natural or synthetic materials including polypropylene, polyethylene, poly(ethylene terephthalate), nylon, paper, cellulose, styrene-isoprene-styrene, styrene-butadiene-styrene block copolymers, the like, or any suitable combination thereof. Some examples of suitable laminates include bilaminates of film and nonwoven such as M18-750 or M18-1018 manufactured by Clopay Corporation, Cincinnati, Ohio. An example of a suitable nonwoven is Typar SBPP3301Y manufactured by BBA Fiberweb™, located in Brentwood, Tenn.

The attachment area 1334 of the present invention, as discussed previously, can be utilized in a number of consumer goods. For example, the attachment area 1334 of the present invention can be joined to a disposable diaper. Any suitable attachment area 1334 elements known in the art can be used in the present invention. Examples of suitable attachment area 1334 elements include engaging components, receiving components, adhesive components, cohesive components, the like, or any suitable combination thereof.

An example of a suitable engaging component may comprise hook fastening material. The hook fastening material can mechanically engage fibrous elements of a receiving element so as to provide a secure closure. A hook fastening material according to the present invention may be manufactured from a wide range of materials. Examples of suitable materials include nylon, polyester, polypropylene, or any combination of these materials, or other materials as are known in the art.

A suitable hook fastening material comprises a number of shaped engaging elements projecting from a backing such as the commercially available material designated Scotchmate™ brand No. FJ3402 available from Minnesota Mining and Manufacturing Company, St. Paul, Minn. Alternatively, the engaging elements may have any shape such as hooks, "T's", mushrooms, or any other shape as are well known in the art. An exemplary hook fastening material is described in U.S. Pat. No. 4,846,815. Another suitable hook fastening material comprises an array of prongs formed of thermoplastic material. Hot melt adhesive thermoplastics, in particular polyester and polyamide hot melt adhesives, are particularly well suited for forming the prongs of the hook fastening material. The prongs, in some embodiments, can be manufactured using a modified gravure printing process by printing the thermoplastic material in its molten state onto a substrate in discrete units, severing the material in a manner that allows stretching of a portion of the thermoplastic material prior to severance, and allowing the stretched molten material to "freeze" resulting in prongs. This hook fastening material and methods and apparatus for making such a hook fastening material are more fully detailed in European Patent Application 0 381 087. In some embodiments, the hooks can be thermoplastically printed. Examples of suitable hook printing processes are described in U.S. Pat. No. 5,540,673 and in WO 2004/082918.

An example of a suitable receiving component may comprise a plurality of loops. Loop fastening material and a method for making the same are described in U.S. Pat. Nos. 5,380,313 ; 5,569,233; 5,407,439; 5,542,942; 5,669,900; 5,318,555; U.S. Application Publication No. 2003/0077430; and WO 04/030763.

An example of a suitable adhesive component may comprise discrete tape tabs. An example of a suitable tape tab is available from the 3M Corporation of St. Paul, Minn., U.S.A. under the designation of XMF99121.

An example of a suitable cohesive component may comprise cohesive fastening patches. In some embodiments, the cohesive fastening patches may be formed of an inherently crystalline water-based synthetic elastomer to which a tackifying agent has been added to disrupt the polycrystalline structure and thereby render the elastomer cohesive. Exemplary synthetic cohesive products are available from Andover Coated Products, Incorporated, of Salisbury, Mass., U.S.A. and are described in U.S. Pat. No. 6,156,424.

Test Methods

Test Sample Preparation & Test Conditions

For all of the following test methods, obtain samples of the articles. Precondition the samples at a temperature of 23° C.±2° C. and 50%±2% relative humidity for at least 2 hours prior to testing. All testing is performed in a conditioned room maintained at a temperature of 23° C.±2° C. and 50%±2% relative humidity.

Test Method for Measuring the Overall Longitudinal Chassis Length

Figure 14:
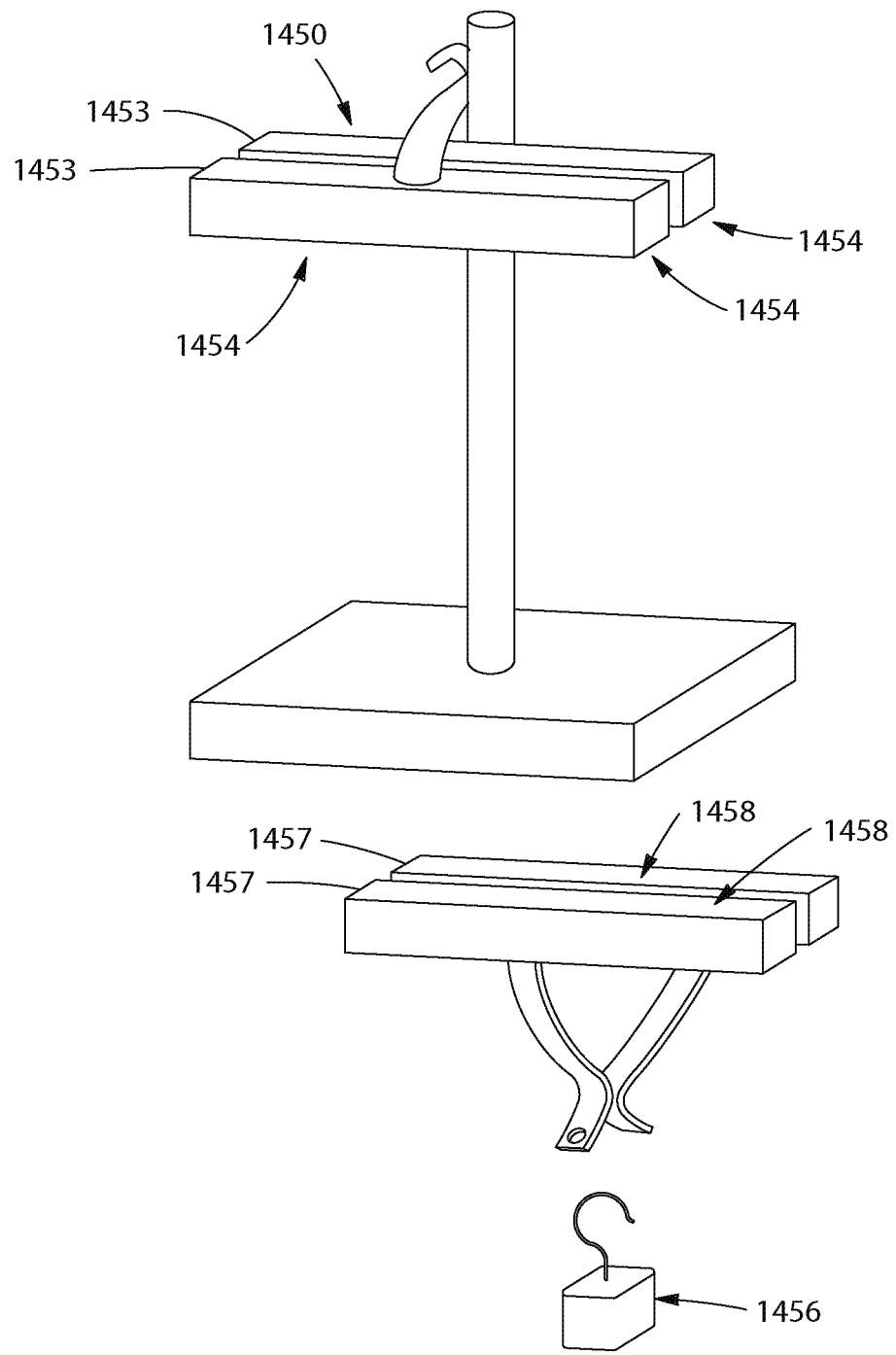
FIG. 14 illustrates a stand for use with a test method of the present disclosure.
Figure 15:
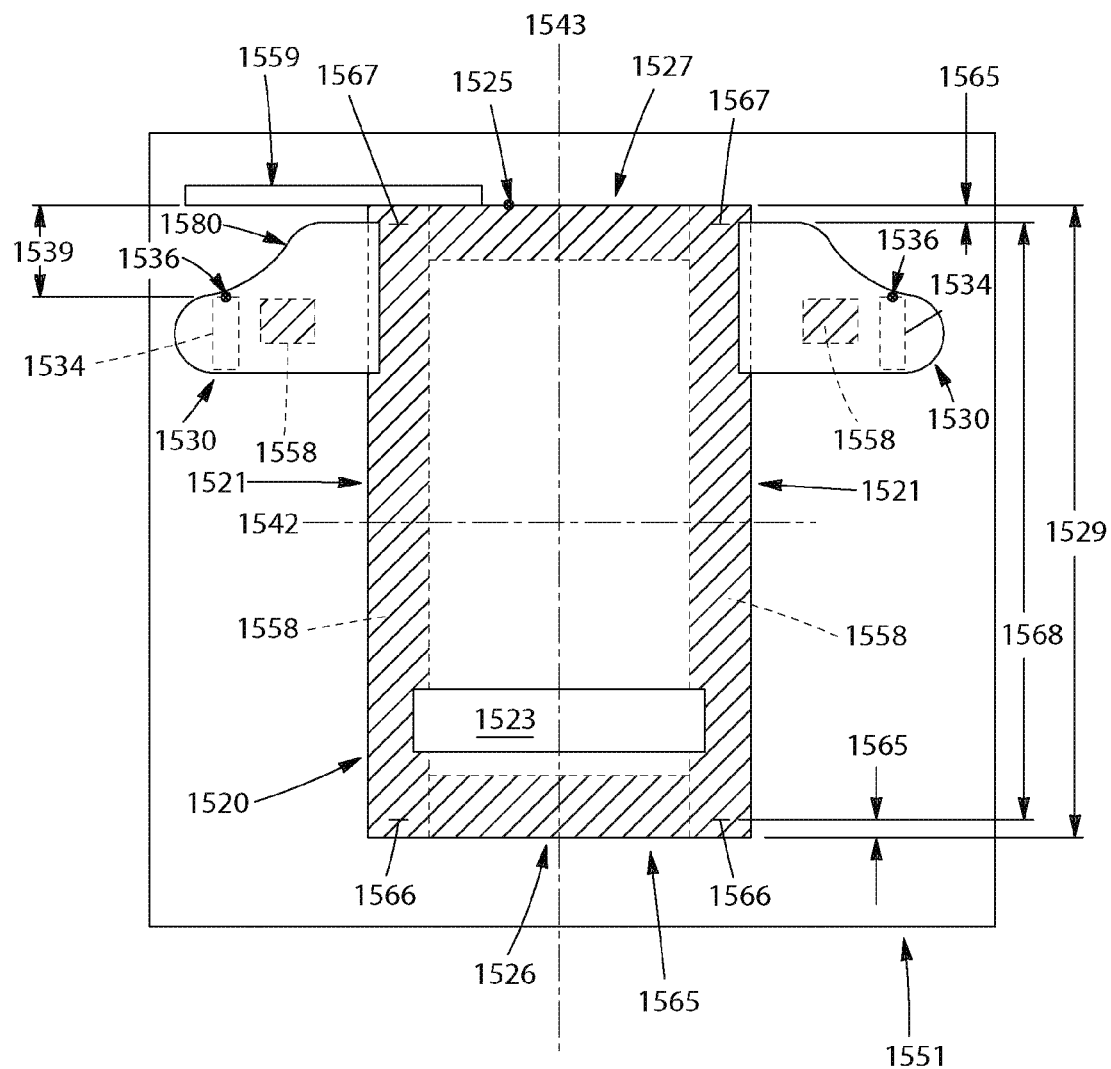
FIG. 15 illustrates a plan view of a front-fastenable wearable absorbent article laid flat for measurements with test methods of the present disclosure.

1. Obtain the required test equipment, which includes:
   a. A ruler calibrated to NIST (National Institute of Standards and Technology). standards, capable of reading to the nearest millimeter.
   b. A stand 1450 as shown in FIG. 14 having upper grips 1453 for securing a front waist edge, lower grips 1457 for securing a back waist edge, and a weight 1456. On the bottom of each of the upper grips 1453 is a downward facing upper grip face 1454 that is horizontally oriented. The upper grips 1453 must be wide enough to span from one front waist edge location 1566 to the other front waist edge location 1566 on an article, as shown in FIG. 15. On the top of each of the lower grips 1457 is an upward facing lower grip face 1458 that is horizontally oriented. The lower grips 1454 must be wide enough to span from one back waist edge location 1567 to the other back waist edge location 1567 on an article, as shown in FIG. 15. The weight 1456 is sized such that the mass of the weight 1456 and the mass of the lower grips 1454 together apply a 10 N load.
2. Obtain samples of the article to be measured, such as the article 1520 of FIG. 15. The elements of the article 1520 are configured in the same way as the like-numbered elements in FIG. 1, except as subsequently described.
3. Using a fine-point pen or marker, mark two front waist edge locations 1566 proximate to the front waist edge 1526. Each of the front waist edge locations 1566 is longitudinally inboard from the farthest longitudinally outboard front waist edge point edge 1565, spaced apart by an offset distance 1565, which is 10 mm. One of the front waist edge locations 1566 should be to one side of the longitudinal centerline 1543 and proximate to one longitudinal edge 1521 of the article 1520. The other front waist edge location 1566 should be on the other side of the longitudinal centerline 1543 and proximate to the other longitudinal edge 1521 of the article 1520. Using the pen or marker, mark two back waist edge locations 1567 proximate to the back waist edge 1527. Each of the back waist edge locations 1567 is longitudinally inboard from the farthest longitudinally inboard point 1525 on the back waist edge 1527, spaced apart by an offset distance 1565, which is 10 mm. One of the back waist edge locations 1567 should be to one side of the longitudinal centerline 1543 and proximate to one longitudinal edge 1521 of the article 1520. The other back waist edge location 1567 should be on the other side of the longitudinal centerline 1543 and proximate to the other longitudinal edge 1521 of the article 1520.
4. For each attachment area 1534, identify the farthest longitudinally outboard attachment area point 1536 and mark that point with the pen or marker.
5. Attach the article 1520 in the stand 1450 of Step 1b, as described below, so the longitudinal centerline 1543 is vertically oriented.
   a. Remove any lateral process-induced contraction present along the front waist edge 1526 (such as that created by a contracted waistband) by pulling in the laterally outboard direction. Secure the front waist edge 1526 in the upper grips 1453, such that the upper grip faces 1463 are vertically aligned (within +/−1 mm) with the two front waist edge locations 1566.
   b. Remove any lateral process-induced contraction present along the back waist edge 1527 (such as that created by a contracted waistband) by pulling in the laterally outboard direction. Secure the back waist edge 1527 in the lower grips 1454, such that the lower grip faces 1464 are vertically aligned (within +/−1 mm) with the two back waist edge locations 1567.
6. Allow the article 1520 to hang freely from the upper grips 1453. Affix the weight 1455 to the lower grips 1454 to apply a 10 N load.
7. Measure the vertical distance 1568 longitudinally from the upper grip face 1463 to the lower grip face 1464 to the nearest millimeter.
8. The overall longitudinal chassis length 1529 is equal to the vertical distance 1568 measured in Step 7 plus 20 millimeters.
9. Test a minimum of ten (n=10) of the same size and kind of article and report the resulting overall longitudinal chassis length as the average of the measurements.

Test Method for Determining the Chassis Edge to Attachment Edge Percentage

1. Obtain the required test equipment, which includes:
   a. A ruler calibrated to NIST standards, capable of reading to the nearest millimeter.
   b. A straight edge, such as straight edge 1559 of FIG. 15.
2. Obtain samples of the article to be measured, such as the article 1520 of FIG. 15.
3. Measure the overall longitudinal chassis length 1529 of the article 1520 as described in the Test Method for Measuring the Overall Longitudinal Chassis Length.
4. Attach the article 1520 to a flat, horizontal surface 1551 with the article 1520 laid flat and having all process-induced contraction pulled out, as shown in FIG. 15. The side ears 1530 should be laid flat in a laterally extended position. The article 1520 may be attached by any suitable attachment means 1558, such as grips, hooks, and/or double-sided tape.
5. Align a straight edge 1559 to coincide with the farthest longitudinally inboard back waist edge point 1525 and parallel to the lateral centerline 1542 of the article 1520.
6. Measure the chassis edge to attachment edge distance 1539 from the straight edge 1559 to the farthest longitudinally outboard attachment area point 1536 to the nearest millimeter.
7. Calculate the chassis edge to attachment edge percentage by dividing the chassis edge to attachment edge distance 1539 by the overall longitudinal chassis length 1529 and multiplying by 100, rounding to the nearest percent. While this test method is illustrated in FIG. 15 as applied to the side ear on the left hand side of the article, this test method is applicable to a side ear on either side of the article.
8. Test a minimum of five of the same size and kind of article, taking measurements on both side ears, for a minimum of ten measurements (n=10) and report the chassis edge to attachment edge percentage as the average of the measurements.

Figure 16:
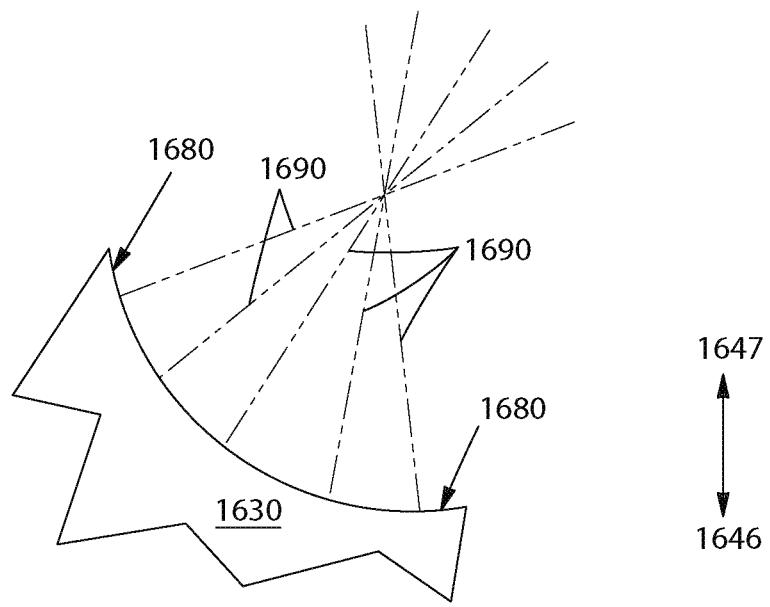
FIG. 16 illustrates a concave portion of an upper edge of a side ear, according to embodiments of the present disclosure.
Figure 17:
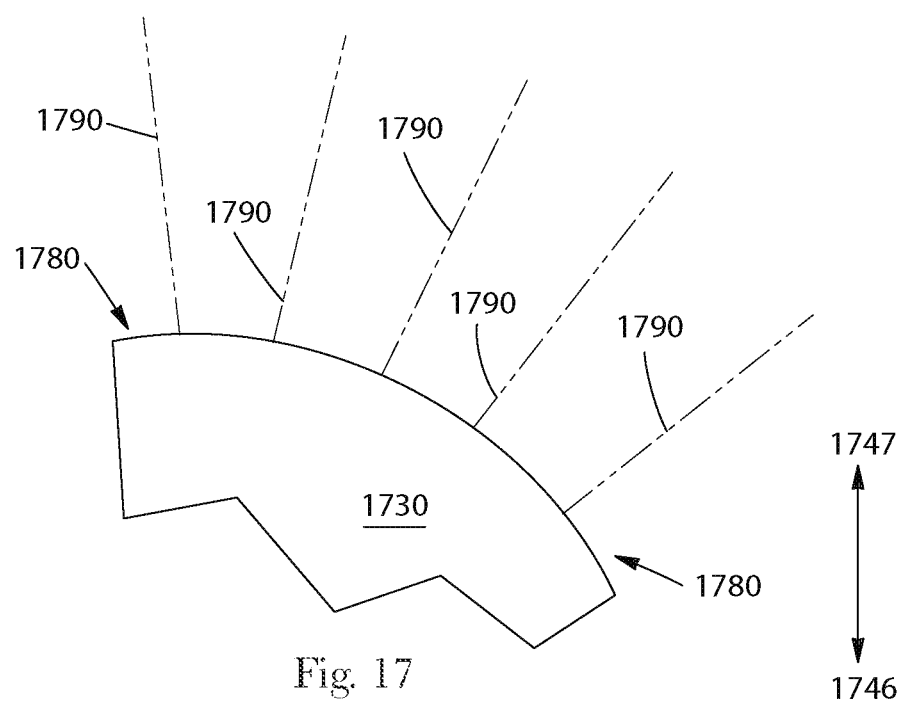
FIG. 17 illustrates a convex portion of an upper edge of a side ear, according to embodiments of the present disclosure.
Figure 18:
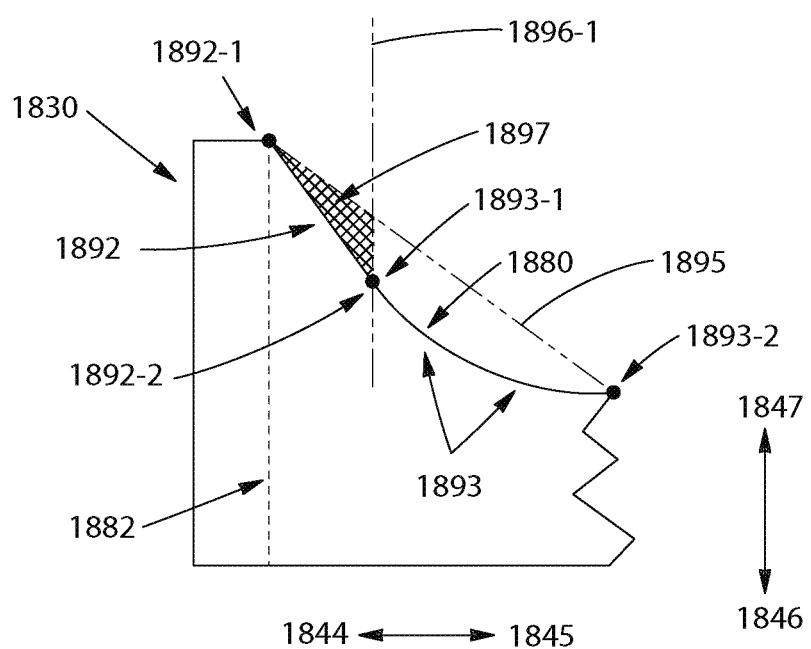
FIG. 18 illustrates a portion of a side ear having an upper edge with a leading continuously straight portion, according to embodiments of the present disclosure.

Test Method for Determining Concave and Convex Portions
1. Obtain the required test equipment, which includes:
   a. A ruler calibrated to NIST standards, capable of reading to the nearest millimeter.
2. Obtain samples of the article to be measured, such as the article 1520 of FIG. 15.
3. Attach the article 1520 to a flat, horizontal surface 1551 with the article 1520 laid flat and having all process-induced contraction pulled out, as shown in FIG. 15. The side ears 1530 should be laid flat in a laterally extended position. The article 1520 may be attached by any suitable attachment means 1558, such as grips, hooks, and/or double-sided tape.
4. Measure the overall lateral dimensions of the regions of the side ear.
   a. An extensible region has an overall lateral dimension that is measured laterally from the first junction line to the first laterally outboard extensible region edge.
   b. An end region has an overall lateral dimension that is measured laterally from the first laterally outboard extensible region edge to the first farthest laterally outboard endpoint.
5. The upper edge of a side ear can have one or more concave portions and/or one or more convex portions. Each continuously curved portion of an upper edge of a side ear is considered to be either concave or convex. In the present disclosure, each part or all of each straight portion of an upper edge of a side ear is also considered to be either concave or convex. Examine the upper edge 1580 of the side ear 1530 to locate all of the concave portions and all of the convex portions, as described below.
6. A portion of an upper edge, which is continuously curved over its entire length, is considered to be concave if neighboring normals, which extend outward from the longitudinally outboard side of the portion, converge. FIG. 16 shows an exemplary continuously curved portion of an upper edge 1680 of a side ear 1630, where neighboring normals 1690, which extend outward from the longitudinally outboard side of the portion, converge. Thus, the portion of the upper edge 1680 in FIG. 16 is concave. Along the upper edge, mark the endpoints for each continuously curved concave portion and then mark that portion as concave.
7. A portion of an upper edge, which is continuously curved over its entire length, is considered to be convex if neighboring normals, which extend outward from the longitudinally outboard side of the portion, diverge. FIG. 17 shows an exemplary continuously curved portion of an upper edge 1780 of a side ear 1730, where neighboring normals 1790, which extend outward from the longitudinally outboard side of the portion, diverge. Thus, the portion of the upper edge 1780 in FIG. 17 is convex. Along the upper edge, mark the endpoints for each continuously curved convex portion and then mark that portion as convex.
8. A portion of an upper edge, which is continuously straight over its entire length, is considered to be either wholly concave, wholly convex, or partly concave and partly convex, as described below.
   a. For a leading continuously straight portion of an upper edge that is immediately adjacent to the junction line, use the following steps, as illustrated with the exemplary embodiment shown in FIG. 18. FIG. 18 illustrates a portion of a side ear 1830 with an upper edge 1880 and a junction line 1882. In FIG. 18, the elements of the side ear 1830 are configured in the same way as the like-numbered elements in FIG. 1, except as subsequently described. The upper edge 1880 includes a leading continuously straight portion 1892 that is immediately adjacent to the junction line 1882.
      i. Identify the inboard and outboard endpoints of the leading continuously straight portion. The inboard endpoint of the leading continuously straight portion will be at the junction line; this is also the inboard endpoint of the upper edge. The outboard endpoint of the leading continuously straight portion will be disposed away from the junction line, at the transition to the immediately adjacent outboard portion. In FIG. 18, the leading continuously straight portion 1892 has inboard endpoint 1892-1 and outboard endpoint 1892-2.
      ii. Identify the immediately adjacent outboard portion. The immediately adjacent outboard portion is the portion of the upper edge that is immediately adjacent to the outboard endpoint of the leading continuously straight portion. The immediately adjacent outboard portion may be a curved concave section, a curved convex section, or another straight section disposed at a non-zero angle with respect to the leading continuously straight section. FIG. 18 shows immediately adjacent outboard portion 1893.
      iii. Identify the inboard and outboard endpoints of the immediately adjacent outboard portion. The inboard endpoint of the immediately adjacent outboard portion will be at the outboard endpoint of the leading continuously straight portion. The outboard endpoint of the immediately adjacent outboard portion will be disposed away from the leading continuously straight portion and relatively closer to the farthest laterally outboard endpoint, at the transition to the next portion or, if there is no next portion, at the outboard endpoint of the upper edge. In FIG. 18, the immediately adjacent outboard portion 1893 has inboard endpoint 1893-1 and outboard endpoint 1893-2. The inboard endpoint 1893-1 coincides with the outboard endpoint 1892-2.

iv. Draw construction lines as follows. First, draw a chord linearly from the inboard endpoint of the leading continuously straight portion to the outboard endpoint of the immediately adjacent outboard portion. Second, draw a longitudinal reference line through the outboard endpoint of the leading continuously straight portion. FIG. 18 shows chord 1895 and longitudinal reference line 1896-1.

v. Identify, a three-sided reference area, in the plane of the ear, formed by the leading continuously straight portion, the chord, and the longitudinal reference line. FIG. 18 shows three-sided reference area 1897, illustrated as a hatched area.

1. If the reference area falls outside of the side ear, then all of the leading continuously straight portion is considered to be a concave portion, according to embodiments of the present disclosure. In FIG. 18, the reference area 1897 falls outside of the side ear 1830, so all of the leading continuously straight portion 1892 is considered to be concave.

Figure 19:
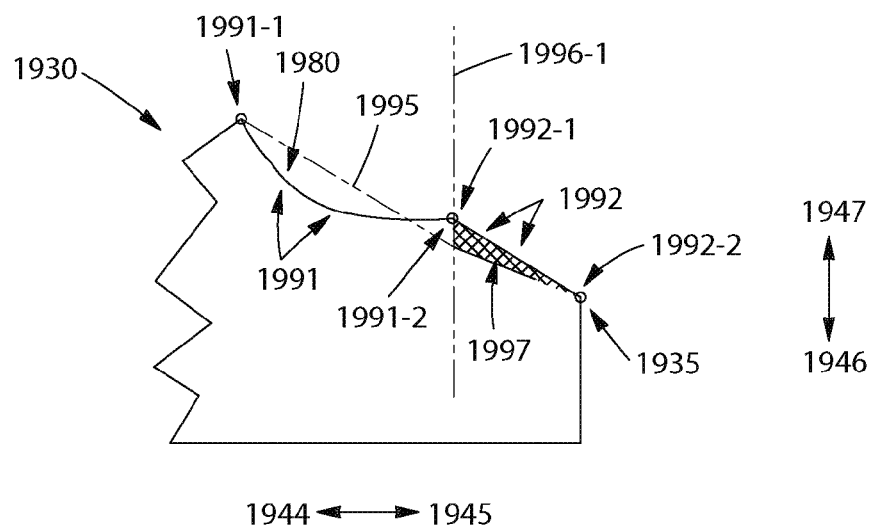
FIG. 19 illustrates a portion of a side ear having an upper edge with a trailing continuously straight portion, according to embodiments of the present disclosure.

2. If the reference area overlaps the side ear, then all of the leading continuously straight portion is considered to be a convex portion, according to embodiments of the present disclosure. In FIG. 18, the reference area 1897 does not overlap the side ear 1830, so the leading continuously straight portion 1892 is not considered to be convex.

vi. Along the upper edge, mark the endpoints of the leading continuously straight portion, then mark the portion as concave or convex, as determined above.

b. For a trailing continuously straight portion of an upper edge that is immediately adjacent to the farthest laterally outboard endpoint, use the following steps, as illustrated with the exemplary embodiment shown in FIG. 19. FIG. 19 illustrates a portion of a side ear 1930 with an upper edge 1980. In FIG. 19, the elements of the side ear 1930 are configured in the same way as the like-numbered elements in FIG. 1, except as subsequently described. The upper edge 1980 includes a trailing continuously straight portion 1992 that is immediately adjacent to the farthest laterally outboard endpoint 1935.

i. Identify the inboard and outboard endpoints of the trailing continuously straight portion. The outboard endpoint of the trailing continuously straight portion will be at the farthest laterally outboard endpoint; this is also the outboard endpoint of the upper edge. The inboard endpoint of the trailing continuously straight portion will be disposed away from the farthest laterally outboard endpoint, at the transition to the immediately adjacent inboard portion. In FIG. 19, the trailing continuously straight portion 1992 has outboard endpoint 1992-2 and inboard endpoint 1992-1.

ii. Identify the immediately adjacent inboard portion. The immediately adjacent inboard portion is the portion of the upper edge that is immediately adjacent to the inboard endpoint of the trailing continuously straight portion. The immediately adjacent inboard portion may be a curved concave section, a curved convex section, or another straight section disposed at a non-zero angle with respect to the trailing continuously straight section. FIG. 19 shows immediately adjacent inboard portion 1991.

iii. Identify the inboard and outboard endpoints of the immediately adjacent inboard portion. The outboard endpoint of the immediately adjacent inboard portion will be at the inboard endpoint of the trailing continuously straight portion. The inboard endpoint of the immediately adjacent inboard portion will be disposed away from the trailing continuously straight portion and relatively closer to the junction line, at the transition to the previous portion or, if there is no previous portion, at the inboard endpoint of the upper edge. In FIG. 19, the immediately adjacent inboard portion 1991 has outboard endpoint 1991-2 and inboard endpoint 1991-1. The outboard endpoint 1991-2 coincides with the inboard endpoint 1992-1.

iv. Draw construction lines as follows. First, draw a chord linearly from the outboard endpoint of the trailing continuously straight portion to the inboard endpoint of the immediately adjacent inboard portion. Second, draw a longitudinal reference line through the inboard endpoint of the trailing continuously straight portion. FIG. 19 shows chord 1995 and longitudinal reference line 1996-1.

v. Identify, a three-sided reference area, in the plane of the ear, formed by the trailing continuously straight portion, the chord, and the longitudinal reference line. FIG. 18 shows three-sided reference area 1997, illustrated as a hatched area.

1. If the reference area falls outside of the side ear, then all of the trailing continuously straight portion is considered to be a concave portion, according to embodiments of the present disclosure. In FIG. 19, the reference area 1997 does not fall outside of the side ear 1930, so the trailing continuously straight portion 1992 is not considered to be concave.

Figure 20:
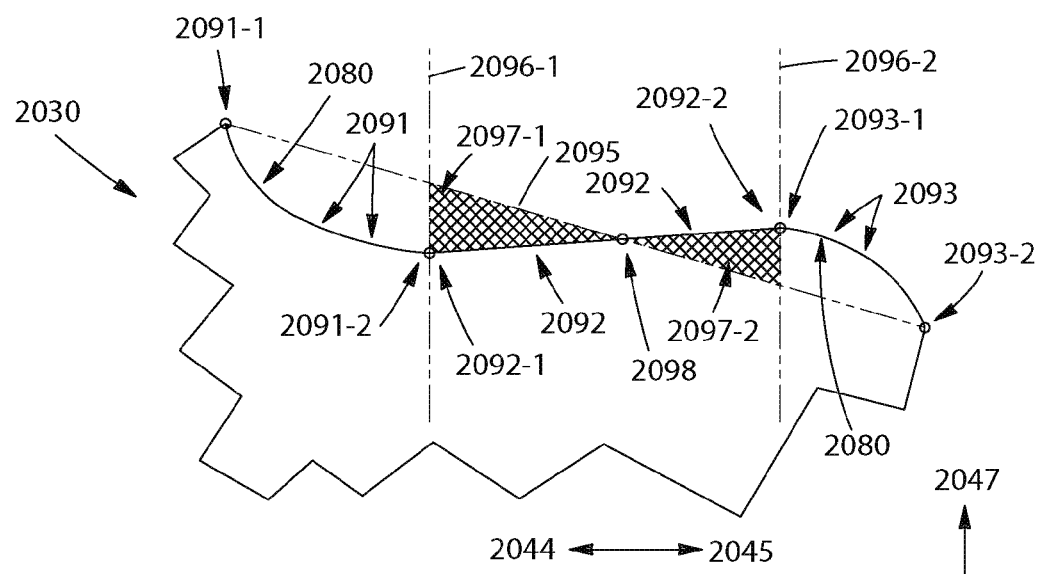
FIG. 20 illustrates a portion of a side ear having an upper edge with an intermediate continuously straight portion, according to embodiments of the present disclosure.

2. If the reference area overlaps the side ear, then all of the trailing continuously straight portion is considered to be a convex portion, according to embodiments of the present disclosure. In FIG. 19, the reference area 1997 overlap the side ear 1930, so the trailing continuously straight portion 1992 is considered to be convex.

vi. Along the upper edge, mark the endpoints of the trailing continuously straight portion, then mark the portion as concave or convex, as determined above.

c. For an intermediate continuously straight portion of an upper edge that is immediately adjacent to and between two other portions of the upper edge, use the following steps, as illustrated with the exemplary embodiment shown in FIG. 20. FIG. 20 illustrates a portion of a side ear 2030 with an upper edge 2080. In FIG. 20, the elements of the side ear 2030 are configured in the same way as the like-numbered elements in FIG. 1, except as subsequently described. The upper edge 2080 includes an intermediate continuously straight portion 2092 that is between an immediately adjacent inboard portion 2091 and an immediately adjacent outboard portion 2093.

i. Identify the inboard and outboard endpoints of the intermediate continuously straight portion. The inboard endpoint of the intermediate continuously straight portion will be relatively closer to the junction line than the outboard endpoint of the intermediate continuously straight portion, when measured along the upper edge. In FIG. 20, the intermediate continuously straight portion 2092 has inboard endpoint 2092-1 and outboard endpoint 2092-2.

ii. Identify the immediately adjacent inboard portion. The immediately adjacent inboard portion is the portion of the upper edge that is immediately adjacent to the inboard endpoint of the intermediate continuously straight portion. The immediately adjacent inboard portion may be a curved concave section, a curved convex section, or another straight section disposed at a non-zero angle with respect to the intermediate continuously straight section. FIG. 20 shows immediately adjacent inboard portion 2091.

iii. Identify the inboard and outboard endpoints of the immediately adjacent inboard portion. The outboard endpoint of the immediately adjacent inboard portion will be at the inboard endpoint of the intermediate continuously straight portion. The inboard endpoint of the immediately adjacent inboard portion will be disposed away from the intermediate continuously straight portion, at the transition to the previous portion or, if there is no previous portion, at the inboard endpoint of the upper edge. In FIG. 20, the immediately adjacent inboard portion 2091 has outboard endpoint 2091-2 and inboard endpoint 2091-1. The outboard endpoint 2091-2 coincides with the inboard endpoint 2092-1.

iv. Identify the immediately adjacent outboard portion. The immediately adjacent outboard portion is the portion of the upper edge that is immediately adjacent to the outboard endpoint of the intermediate continuously straight portion. The immediately adjacent outboard portion may be a curved concave section, a curved convex section, or another straight section disposed at a non-zero angle with respect to the intermediate continuously straight section. FIG. 20 shows immediately adjacent outboard portion 2093.

v. Identify the inboard and outboard endpoints of the immediately adjacent outboard portion. The inboard endpoint of the immediately adjacent outboard portion will be at the outboard endpoint of the intermediate continuously straight portion. The outboard endpoint of the immediately adjacent outboard portion will be disposed away from the intermediate continuously straight portion, at the transition to the next portion or, if there is no next portion, at the outboard endpoint of the upper edge. In FIG. 20, the immediately adjacent outboard portion 2093 has inboard endpoint 2093-1 and outboard endpoint 2093-2. The inboard endpoint 2093-1 coincides with the outboard endpoint 2092-2.

vi. Draw construction lines as follows. First, draw a chord linearly from the inboard endpoint of the immediately adjacent inboard portion to the outboard endpoint of the immediately adjacent outboard portion. Second, draw a first longitudinal reference line through the inboard endpoint of the intermediate continuously straight portion and draw a second longitudinal reference line through the outboard endpoint of the intermediate continuously straight portion. FIG. 20 shows chord 2095, first longitudinal reference line 2096-1, and second longitudinal reference line 2096-2.

vii. Identify, reference areas(s), in the plane of the ear, formed by the intermediate continuously straight portion, the chord, the first longitudinal reference line, and the second reference.

1. In embodiments where the chord does not intersect the intermediate continuously straight portion, there will be one four-sided reference area. In FIG. 20, there are two three-sided reference areas, as described below.

a. If the reference area falls outside of the side ear, then all of the trailing continuously straight portion is considered to be a concave portion, according to embodiments of the present disclosure.

b. If the reference area overlaps the side ear, then all of the trailing continuously straight portion is considered to be a convex portion, according to embodiments of the present disclosure.

c. Along the upper edge, mark the endpoints of the intermediate continuously straight portion, then mark the portion as concave or convex, as determined above.

2. In embodiments where the chord intersects the intermediate continuously straight portion, there will be two three-sided reference areas. The first three-sided reference area will be formed by a first part of the intermediate continuously straight portion, a first part of the chord, and the first longitudinal reference line. The second three-sided reference area will be formed by a second part of the intermediate continuously straight portion, a second part of the chord, and the second longitudinal reference line. In FIG. 20, the chord 2095 intersects the intermediate continuously straight portion 2092 at intersection 2098, so there are two three-sided reference areas; the first three-sided reference area is 2097-1 and the second three-sided reference area is 2097-2.

a. For the reference area that falls outside of the side ear, the part of the intermediate continuously straight portion that forms a side of that outside area is considered to be a concave portion, according to embodiments of the present disclosure. In FIG. 20, the first reference area 2097-1 falls outside of the side ear 2030 so the part of the intermediate continuously straight portion 2092 that forms a side of the first reference area 2097-1 is considered to be a concave portion. Thus, the laterally inboard part of the intermediate continuously straight portion 2092, from the inboard endpoint 2092-1 to the intersection 2098, is considered to be a concave portion.

b. For the reference area that falls inside of the side ear, the part of the intermediate continuously straight portion that forms a side of that inside area is considered to be a convex portion, according to embodiments of the present disclosure. In FIG. 20, the second reference area 2097-2 falls inside of the side ear 2030 so the part of the intermediate continuously straight portion 2092 that forms a side of the second reference area 2097-2 is considered to be a convex portion. Thus, the laterally outboard part of the intermediate continuously straight portion 2092, from the intersection 2098 to the outboard endpoint 2092-2, is considered to be a convex portion.

c. Along the upper edge, mark the endpoints of the intermediate continuously straight portion and the intersection between the chord and the upper edge, then mark the concave portion and the convex portion, as determined above.

Test Method for Determining Concave and Convex Dimensions and Percentages

1. Obtain the required test equipment, which includes a ruler calibrated to NIST (National Institute of Standards and Technology). standards, capable of reading to the nearest millimeter.
2. Measure the overall lateral dimension of the upper edge of the side ear by measuring laterally from the junction line to the farthest laterally outboard endpoint.
3. Measure the overall lateral dimension of the laterally extensible region upper edge portion by measuring laterally from the junction line to the laterally outboard extensible region edge.
4. Measure the overall lateral dimension of the end region by measuring laterally from the outboard extensible region edge to the farthest laterally outboard endpoint. Together, the overall lateral dimension of the laterally extensible region upper edge portion and the overall lateral dimension of the end region, when measured for the same side ear should equal the overall lateral dimension of the upper edge of the side ear.
5. Determine the total concave lateral dimension of the laterally extensible region by adding together the overall lateral dimension of each and every concave portion within the laterally extensible region upper edge portion, including the overall lateral dimension of any part or whole of a straight portion that is considered to be concave, as determined by the Test Method for Determining Concave and Convex Portions. If a concave portion is only partly disposed within the laterally extensible region upper edge portion, then the overall lateral dimension of only the part that is disposed within the laterally extensible region upper edge portion should be included in the total. If there is no concave portion within the laterally extensible region upper edge portion, then the total concave lateral dimension of the laterally extensible region is zero.
6. Determine the total convex lateral dimension of the laterally extensible region by adding together the overall lateral dimension of each and every convex portion within the laterally extensible region upper edge portion, including the overall lateral dimension of any part or whole of a straight portion that is considered to be convex, as determined by the Test Method for Determining Concave and Convex Portions. If a convex portion is only partly disposed within the laterally extensible region upper edge portion, then the overall lateral dimension of only the part that is disposed within the laterally extensible region upper edge portion should be included in the total. If there is no convex portion within the laterally extensible region upper edge portion, then the total convex lateral dimension of the laterally extensible region is zero. Together, the total concave lateral dimension of the laterally extensible region upper edge portion and the total convex lateral dimension of the laterally extensible region upper edge portion, when measured for the same side ear should equal the overall lateral dimension of the laterally extensible region upper edge portion of the side ear.
7. Determine the total concave lateral dimension of the end region by adding together the overall lateral dimension of each and every concave portion within the end region upper edge portion, including the overall lateral dimension of any part or whole of a straight portion that is considered to be concave, as determined by the Test Method for Determining Concave and Convex Portions. If a concave portion is only partly disposed within the end region upper edge portion, then the overall lateral dimension of only the part that is disposed within the end region upper edge portion should be included in the total. If there is no concave portion within the end region upper edge portion, then the total concave lateral dimension of the end region is zero.
8. Determine the total convex lateral dimension of the end region by adding together the overall lateral dimension of each and every convex portion within the end region upper edge portion, including the overall lateral dimension of any part or whole of a straight portion that is considered to be convex, as determined by the Test Method for Determining Concave and Convex Portions. If a convex portion is only partly disposed within the end region upper edge portion, then the overall lateral dimension of only the part that is disposed within the end region upper edge portion should be included in the total. If there is no convex portion within the end region upper edge portion, then the total convex lateral dimension of the end region is zero. Together, the total concave lateral dimension of the end region upper edge portion and the total convex lateral dimension of the end region upper portion, when measured for the same side ear should equal the overall lateral dimension of the end region upper edge portion of the side ear.
9. Determine the overall lateral dimension of a single continuous concave portion in the end region by adding together the overall lateral dimensions of all of the concave portions that are immediately adjacent to each other and are within the end region upper edge portion, including the overall lateral dimensions of any part or whole of straight portions that are considered to be concave, as determined by the Test Method for Determining Concave and Convex Portions. If a concave portion is only partly disposed within the end region upper edge portion, then the overall lateral dimension of only the part that is disposed within the end region upper edge portion should be included in the overall lateral dimension of the single continuous concave portion. If the entire end region upper edge portion is formed by concave portions that are immediately adjacent to each other, then the overall lateral dimension of the single continuous concave portion is equal to the overall lateral dimension of the end region upper edge portion.
10. Determine the overall lateral dimension of a single continuous convex portion in the end region by adding together the overall lateral dimensions of all of the convex portions that are immediately adjacent to each other and are within the end region upper edge portion, including the overall lateral dimensions of any part or whole of straight portions that are considered to be convex, as determined by the Test Method for Determining Convex and Convex Portions. If a convex portion is only partly disposed within the end region upper edge portion, then the overall lateral dimension of only the part that is disposed within the end region upper edge portion should be included in the overall lateral dimension of the single continuous convex portion. If the entire end region upper edge portion is formed by convex portions that are immediately adjacent to each other, then the overall lateral dimension of the single continuous convex portion is equal to the overall lateral dimension of the end region upper edge portion.
11. To calculate a percentage value, as described herein, divide the measurement of the portion of the whole by the measurement of the whole and multiply the result by 100. For example, to calculate the total concave lateral dimension of the laterally extensible region as a percentage of the laterally extensible region, divide the total concave lateral dimension of the laterally extensible region by the overall lateral dimension of the laterally extensible region upper edge portion and multiply the result by 100.
12. For each dimension or percentage value, test a minimum of five of the same size and kind of article, taking measurements on both side ears, for a minimum of ten measurements (n=10) and report the value as the average of the values.

For obtaining results for a selected product for purposes herein, test a minimum of ten samples (n=10) and report each result as an average.

The present disclosure contemplates that the various embodiments disclosed herein can be used in combination with various additional and/or alternate structures of absorbent articles, as will be understood by one of skill in the art.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any disclosure disclosed or claimed herein or that it alone, or in any combination with any other reference or references, teaches, suggests or discloses any such disclosure. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. An array of front-fastenable disposable wearable absorbent articles, the array comprising:
a first front-fastenable disposable wearable absorbent article including a first side ear having a first side ear end region with a first end region upper edge portion, the first end region upper edge portion having a first end region upper edge overall lateral dimension, an inboard endpoint, and an outboard endpoint,
wherein the first end region upper edge portion has at least one first concave portion forming a first total concave lateral dimension that is at least 25% of the first end region upper edge overall lateral dimension, and from the inboard endpoint to the laterally outboard end, the first end region upper edge portion only has slopes less than or equal to zero; and
a second front-fastenable disposable wearable absorbent article including a second side ear having a second side ear end region with a second end region upper edge portion,
wherein the second end region upper edge portion having a second end region upper edge overall lateral dimension, and wherein the second end region upper edge portion has at least one second convex portion forming a second total convex lateral dimension that is at least 25% of the second end region upper edge overall lateral dimension,
wherein the second wearer size is one greater than the first wearer size;
the first front-fastenable disposable wearable absorbent article includes a first chassis with a first back waist edge and a first overall longitudinal chassis length, the first chassis is joined to the first side ear, the first side ear has a first attachment area, the first back waist edge has a first farthest longitudinally inboard back waist edge point, the first attachment area has a first farthest longitudinally outboard attachment area point, the first article has a first chassis edge to attachment edge distance measured longitudinally from the first farthest longitudinally inboard back waist edge point to the first farthest longitudinally outboard attachment area point, and the first article has a first chassis edge to attachment edge percentage, which is the first chassis edge to attachment edge distance expressed as a percentage of the first overall longitudinal chassis length; and
the second front-fastenable disposable wearable absorbent article includes a second chassis with a second back waist edge and a second overall longitudinal chassis length, the second chassis is joined to the second side ear, the second side ear has a second attachment area, the second back waist edge has a second farthest longitudinally inboard back waist edge point, the second attachment area has a second farthest longitudinally outboard attachment area point, the second article has a second chassis edge to attachment edge distance measured longitudinally from the second farthest longitudinally inboard back waist edge point to the second farthest longitudinally outboard attachment area point, and the second article has a second chassis edge to attachment edge percentage, which is the second chassis edge to attachment edge distance expressed as a percentage of the second overall longitudinal chassis length;
wherein the first chassis edge to attachment edge percentage is at least 1.5 percentage points greater than the second chassis edge to attachment edge percentage.

2. The array of claim 1, wherein the first total concave lateral dimension is at least 50% of the first end region upper edge overall lateral dimension.

3. The array of claim 1, wherein the first end region upper edge portion includes a single continuous first concave portion that is at least 50% of the first end region upper edge overall lateral dimension.

4. The array of claim 1, wherein the second total convex lateral dimension is at least 50% of the second end region upper edge overall lateral dimension.

5. The array of claim 1, wherein the second end region upper edge portion includes a single continuous second convex portion that is at least 50% of the second end region upper edge overall lateral dimension.

6. The array of claim 1, wherein the first end region upper edge portion only has slopes less than zero.

7. The array of claim 1, wherein:
at least part of the first end region upper edge portion has a first overall contour;
the first article has a first front waist edge; and
when the first article is formed for wearing, a first portion of the first front waist edge is proximate to the part of the first end region upper edge portion, and the first portion has a first waist edge overall contour that is substantially the same as the first overall contour.

8. The array of claim 7, wherein:
at least part of the second end region upper edge portion has a second overall contour;
the second article has a second front waist edge; and
when the second article is formed for wearing, a second portion of the second front waist edge is proximate to the part of the second end region upper edge portion, and the second portion has a second waist edge overall contour that is substantially the same as the second overall contour.

9. The array of claim 1, wherein the first wearer size corresponds with a first wearer that is an immobile newborn.

10. The array of claim 1, wherein the second wearer size corresponds with a second wearer that is a mobile baby.

11. The array of claim 1, wherein the first side ear is integrally-formed and the second side ear is integrally-formed.

12. An array of front-fastenable disposable wearable absorbent articles, the array comprising:
a first front-fastenable disposable wearable absorbent article sized for a first wearer size and including a first side ear having a first side ear end region with a first end region upper edge portion, the first end region upper edge portion having a first end region upper edge overall lateral dimension,
wherein the first end region upper edge portion has at least one first concave portion forming a first total concave lateral dimension that is at least 50% of the first end region upper edge overall lateral dimension; and
a second front-fastenable disposable wearable absorbent article sized for a second wearer size that is greater than the first wearer size and including a second side ear having a second side ear end region with a second end region upper edge portion, the second end region upper edge portion having a second end region upper edge overall lateral dimension,
wherein the second end region upper edge portion has at least one second convex portion forming a second total convex lateral dimension that is at least 50% of the second end region upper edge overall lateral dimension,
wherein the first front-fastenable disposable wearable absorbent article includes a first chassis with a first back waist edge and a first overall longitudinal chassis length, the first chassis is joined to the first side ear, the first side ear has a first attachment area, the first back waist edge has a first farthest longitudinally inboard back waist edge point, the first attachment area has a first farthest longitudinally outboard attachment area point, the first article has a first chassis edge to attachment edge distance measured longitudinally from the first farthest longitudinally inboard back waist edge point to the first farthest longitudinally outboard attachment area point, and the first article has a first chassis edge to attachment edge percentage, which is the first chassis edge to attachment edge distance expressed as a percentage of the first overall longitudinal chassis length;
wherein the second front-fastenable disposable wearable absorbent article includes a second chassis with a second back waist edge and a second overall longitudinal chassis length, the second chassis is joined to the second side ear, the second side ear has a second attachment area, the second back waist edge has a second farthest longitudinally inboard back waist edge point, the second attachment area has a second farthest longitudinally outboard attachment area point, the second article has a second chassis edge to attachment edge distance measured longitudinally from the second farthest longitudinally inboard back waist edge point to the second farthest longitudinally outboard attachment area point, and the second article has a second chassis edge to attachment edge percentage, which is the second chassis edge to attachment edge distance expressed as a percentage of the second overall longitudinal chassis length; and
wherein the first chassis edge to attachment edge percentage is at least 1.5 percentage points greater than the second chassis edge to attachment edge percentage.

13. The array of claim 12, wherein:
the first side ear has a first side ear laterally extensible region adjacent to the first side ear end region, the first side ear laterally extensible region having a first laterally extensible region upper edge portion;
wherein the first laterally extensible region upper edge portion has at least one first concave portion forming a first total concave lateral dimension that is at least 25% of the first laterally extensible region upper edge overall lateral dimension; and
the second side ear has a second side ear laterally extensible region adjacent to the second side ear end region, the second side ear laterally extensible region having a second laterally extensible region upper edge portion:
wherein the second laterally extensible region upper edge portion has at least one second convex portion forming a second total convex lateral dimension that is at least 25% of the second laterally extensible region upper edge overall lateral dimension.

14. The array of claim 12, further comprising a third front-fastenable disposable wearable absorbent article sized for a third wearer size that is greater than the first wearer size and is less than the second wearer size, and including a third side ear having a third side ear end region with a third end region upper edge portion, the third end region upper edge portion having a third end region upper edge overall lateral dimension;
wherein the third end region upper edge portion has:
at least one third concave portion forming a third total concave lateral dimension that is less than 50% of the third end region upper edge overall lateral dimension; and
at least one third convex portion forming a third total convex lateral dimension that is less than 50% of the third end region upper edge overall lateral dimension.

15. The array of claim 12, wherein the first total concave lateral dimension is at least 75% of the first end region upper edge overall lateral dimension.

16. The array of claim 12, wherein the second total convex lateral dimension is at least 75% of the second end region upper edge overall lateral dimension.

17. The array of claim 12, wherein the first end region upper edge portion includes a single continuous first concave portion that is at least 50% of the first end region upper edge overall lateral dimension.

18. The array of claim 12, wherein the second end region upper edge portion includes a single continuous second convex portion that is at least 50% of the second end region upper edge overall lateral dimension.

19. An array of front-fastenable disposable wearable absorbent articles, the array comprising:
- a first front-fastenable disposable wearable absorbent article sized for a first wearer size and including a first side ear having a first side ear end region with a first end region upper edge portion; the first end region upper edge portion having a first end region upper edge overall lateral dimension;
- wherein the first end region upper edge portion has:
  - at least one first concave portion forming a first total concave lateral dimension that is at least 25% of the first end region upper edge overall lateral dimension; and
  - at least one first convex portion forming a first total convex lateral dimension that is less than 25% of the first end region upper edge overall lateral dimension; and
- a second front-fastenable disposable wearable absorbent article sized for a second wearer size that is greater than the first wearer size and including a second side ear having a second side ear end region with a second end region upper edge portion; the second end region upper edge portion having a second end region upper edge overall lateral dimension;
- wherein the second end region upper edge portion has:
  - at least one second convex portion forming a second total convex lateral dimension that is at least 25% of the second end region upper edge overall lateral dimension; and
  - at least one second concave portion forming a second total concave lateral dimension that is less than 25% of the second end region upper edge overall lateral dimension,
- wherein the first front-fastenable disposable wearable absorbent article includes a first chassis with a first back waist edge and a first overall longitudinal chassis length, the first chassis is joined to the first side ear, the first side ear has a first attachment area, the first back waist edge has a first farthest longitudinally inboard back waist edge point, the first attachment area has a first farthest longitudinally outboard attachment area point, the first article has a first chassis edge to attachment edge distance measured longitudinally from the first farthest longitudinally inboard back waist edge point to the first farthest longitudinally outboard attachment area point, and the first article has a first chassis edge to attachment edge percentage, which is the first chassis edge to attachment edge distance expressed as a percentage of the first overall longitudinal chassis length;
- wherein the second front-fastenable disposable wearable absorbent article includes a second chassis with a second back waist edge and a second overall longitudinal chassis length, the second chassis is joined to the second side ear, the second side ear has a second attachment area, the second back waist edge has a second farthest longitudinally inboard back waist edge point, the second attachment area has a second farthest longitudinally outboard attachment area point, the second article has a second chassis edge to attachment edge distance measured longitudinally from the second farthest longitudinally inboard back waist edge point to the second farthest longitudinally outboard attachment area point, and the second article has a second chassis edge to attachment edge percentage, which is the second chassis edge to attachment edge distance expressed as a percentage of the second overall longitudinal chassis length; and
- wherein the first chassis edge to attachment edge percentage is at least 1.5 percentage points greater than the second chassis edge to attachment edge percentage.

* * * * *